(12) United States Patent
May et al.

(10) Patent No.: US 8,118,868 B2
(45) Date of Patent: Feb. 21, 2012

(54) METHOD AND APPARATUS FOR ATTACHING SOFT TISSUE TO AN IMPLANT

(75) Inventors: Brian M. May, Warsaw, IN (US); Jason D. Meridew, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 342 days.

(21) Appl. No.: 12/398,548

(22) Filed: Mar. 5, 2009

(65) Prior Publication Data

US 2009/0265014 A1   Oct. 22, 2009

Related U.S. Application Data

(63) Continuation-in-part of application No. 12/107,437, filed on Apr. 22, 2008, now abandoned.

(51) Int. Cl.
*A61F 2/08* (2006.01)
(52) U.S. Cl. .................................. 623/13.14; 623/22.11
(58) Field of Classification Search ............... 623/13.14, 623/22.11, 22.15; 606/70
See application file for complete search history.

(56) References Cited

U.S. PATENT DOCUMENTS

| | | | |
|---|---|---|---|
| 4,344,193 A | 8/1982 | Kenny | |
| 4,597,766 A | 7/1986 | Hilal et al. | |
| 4,770,663 A | 9/1988 | Hanslik et al. | |
| 4,773,910 A | 9/1988 | Chen et al. | |
| 4,823,780 A | 4/1989 | Odensten et al. | |
| 4,919,667 A | 4/1990 | Richmond | |
| 5,002,545 A | 3/1991 | Whiteside et al. | |
| 5,002,574 A | 3/1991 | May et al. | |
| 5,067,962 A | 11/1991 | Campbell et al. | |
| 5,112,335 A | 5/1992 | Laboureau et al. | |
| 5,282,867 A | 2/1994 | Mikhail | |
| 5,385,567 A | 1/1995 | Goble | |
| 5,498,302 A | 3/1996 | Davidson | |
| 5,534,033 A | 7/1996 | Simpson | |
| 5,562,664 A | 10/1996 | Durlacher et al. | |
| 5,776,200 A | 7/1998 | Johnson et al. | |
| 5,782,925 A | 7/1998 | Collazo et al. | |
| 5,989,294 A | 11/1999 | Marlow et al. | |
| 6,004,351 A | 12/1999 | Tomita et al. | |

(Continued)

FOREIGN PATENT DOCUMENTS

DE   29922088   4/2000

(Continued)

OTHER PUBLICATIONS

"MalloryHead™ Modular Calcar Revision System," Biomet Orthopedics, Inc., (2006) pp. 1-16.

(Continued)

*Primary Examiner* — Thomas J Sweet
*Assistant Examiner* — Matthew Schall
(74) *Attorney, Agent, or Firm* — Harness, Dickey

(57) ABSTRACT

A system and method for attaching soft tissue to a prosthetic implant can include a prosthetic component that defines a soft tissue attachment region having an attachment surface thereon. A first construct can be formed of porous metal and be removably coupled to the attachment surface. A second construct can be positioned outboard of the soft tissue. A fastener can be engaged to the second construct capturing the soft tissue against the first construct. The fastener can be coupled on a distal end to the first prosthetic component.

21 Claims, 18 Drawing Sheets

U.S. PATENT DOCUMENTS

| | | |
|---|---|---|
| 6,004,352 A | 12/1999 | Buni |
| 6,127,596 A | 10/2000 | Brown et al. |
| 6,200,685 B1 | 3/2001 | Davidson |
| 6,203,576 B1 | 3/2001 | Afriat et al. |
| 6,221,107 B1 | 4/2001 | Steiner et al. |
| 6,235,058 B1 | 5/2001 | Huene |
| 6,302,915 B1 | 10/2001 | Cooney, III et al. |
| 6,458,161 B1 | 10/2002 | Gibbs et al. |
| 6,592,622 B1 | 7/2003 | Ferguson |
| 6,629,997 B2 | 10/2003 | Mansmann |
| 6,905,513 B1 | 6/2005 | Metzger |
| 7,001,429 B2 | 2/2006 | Ferguson |
| 7,153,327 B1 | 12/2006 | Metzger |
| 7,179,259 B1 * | 2/2007 | Gibbs .................. 606/64 |
| 7,255,715 B2 | 8/2007 | Metzger |
| 7,291,177 B2 | 11/2007 | Gibbs |
| 2002/0077629 A1 * | 6/2002 | Hoffman et al. ............ 606/59 |
| 2004/0260296 A1 | 12/2004 | Kaiser et al. |
| 2005/0021148 A1 | 1/2005 | Gibbs |
| 2005/0171604 A1 | 8/2005 | Michalow |
| 2006/0241776 A1 | 10/2006 | Brown et al. |
| 2006/0241781 A1 | 10/2006 | Brown et al. |
| 2007/0129809 A1 | 6/2007 | Meridew et al. |
| 2007/0173948 A1 | 7/2007 | Meridew et al. |
| 2007/0244565 A1 | 10/2007 | Stchur |
| 2007/0250175 A1 | 10/2007 | Meridew et al. |
| 2008/0147187 A1 | 6/2008 | Bollinger et al. |
| 2008/0217263 A1 | 9/2008 | Higgins et al. |
| 2008/0281428 A1 | 11/2008 | Meyers et al. |
| 2009/0084491 A1 | 4/2009 | Uthgenannt et al. |
| 2009/0216325 A1 | 8/2009 | May et al. |

FOREIGN PATENT DOCUMENTS

| | | |
|---|---|---|
| FR | 2634373 A1 | 1/1990 |
| FR | 2663837 A1 | 1/1992 |
| FR | 2734709 A1 | 12/1996 |
| GB | 2129306 A | 5/1984 |
| JP | 0127672 A | 5/1998 |
| RU | 2051647 C1 | 1/1996 |
| RU | 2076667 C1 | 4/1997 |

OTHER PUBLICATIONS

International Search Report and Written Opinion mailed Jul. 30, 2009 for PCT/US2009/039580 claiming benefit of U.S. Appl. No. 12/107,437, filed Apr. 22, 2008.

Declaration of John White regarding PSCD and Customized Device and Exhibits 1-5.

International Preliminary Report on Patentability and Written Opinion mailed Nov. 4, 2010 for PCT/US2009/039580 claiming benefit of U.S. Appl. No. 12/107,437, filed Apr. 22, 2008.

* cited by examiner

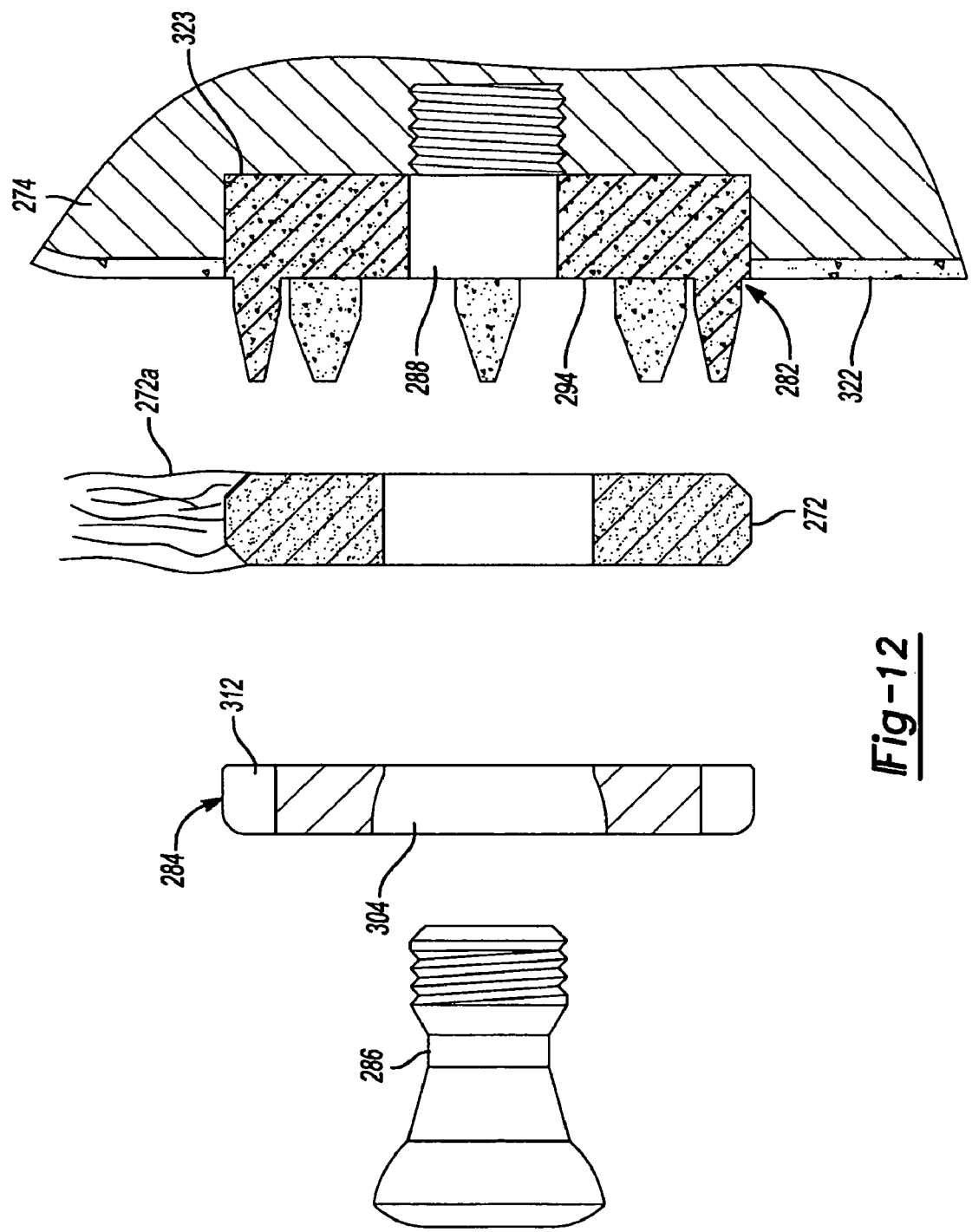

METHOD AND APPARATUS FOR ATTACHING SOFT TISSUE TO AN IMPLANT

CROSS-REFERENCE TO RELATED APPLICATIONS

This application is a continuation-in-part of U.S. patent application Ser. No. 12/107,437, filed on Apr. 22, 2008. The disclosure of the above application is incorporated herein by reference.

FIELD

The present disclosure relates to endoscopic soft tissue fixation. More particularly, the present disclosure relates to an apparatus and a method for securing soft tissue to bone.

INTRODUCTION

Ligaments and tendons are soft collagenous tissues. Ligaments are strong fibrous connective soft tissue, which connect the articular ends of bones to bind them together and to facilitate or limit motion. Tendons connect muscle to bone. Injuries to ligaments are common, and patients who are physically active are generally more susceptible to such ligament injuries. The anterior cruciate ligament (ACL) of the knee joint is a ligament frequently injured by such patients. Such injuries cause instability in the knee joint which, when left untreated, may lead to degenerative arthritis. Because of this condition, ACL reconstruction may be required. Generally during ACL reconstruction, a substitute soft tissue ligament or graft can be attached to the femur and/or tibia to facilitate regrowth and permanent attachment. The medial collateral ligament (MCL) and the lateral collateral ligament (LCL) are other ligaments associated with the knee that can become injured. Generally, injuries to the MCL occur more frequently than injuries to other ligaments of the knee. Isolated injuries of the LCL are less common and typically occur in association with ACL or posterior cruciate ligament (PCL) injuries.

When an injury (i.e., a tear) to any of these ligaments occurs, a surgical procedure can often be performed to repair the injury. During such a procedure it may be necessary to attach soft tissue (such as the host ligament, or a replacement graft) to bone. When using a replacement graft, the graft may usually be taken from the hamstring ligament, specifically, the semitendinosus and gracilis ligaments or tendons. When repairing an ACL or PCL, such grafts may generally be fed through a ligament tunnel and secured outside the tunnel. The graft is generally secured by a non-endoscopic means of stapling or screwing the graft onto the outside surface of the tibia and/or femur.

In other examples, it may be necessary to reattach damaged or deficient ligaments to a total joint replacement component during implantation of a given replacement prosthesis. In instances where femoral replacement is necessary but some or all of the MCL, LCL and/or PCL are intact; it may be suitable to implant a cruciate retaining femoral component. In some examples, it may be desirable to reattach ligaments to preserve host bone, reduce trauma to the patient and prolong the need for more constraining devices.

SUMMARY

An assembly for attaching soft tissue to a prosthetic implant can include a prosthetic component that defines a soft tissue attachment region having an attachment surface thereon. A first construct can be formed of porous metal and be removably coupled to the attachment surface. A second construct can be positioned outboard of the soft tissue. A fastener can be engaged to the second construct and capture the soft tissue against the first construct. The fastener can be coupled on a distal end to the first prosthetic component.

According to additional features, the prosthetic component can be a femoral prosthesis. The first construct can define a first washer having a first aperture formed therein. The first washer can define a plurality of extension portions formed on an outboard surface that extend in a direction away from the prosthetic component. The second construct can define a second washer having a second aperture formed therein. The second washer can define notches formed therein, wherein the plurality of extension portions extend through the notches in an assembled position. According to one example, the notches can be defined around a perimeter of the second washer. The fastener can threadably engage a threaded bore formed in the prosthetic component in an assembled position.

According to additional features, the extension portions can pierce the soft tissue in an assembled position. The extension portions can define spikes according to one example or raised walls according to another example. According to one example, the first and second washers can each define an arcuate shaped body that conforms to the attachment surface of the prosthetic component. The soft tissue attachment region can be defined on a lateral surface of a lateral condyle of the femoral prosthesis and the soft tissue can be a lateral collateral ligament (LCL). According to additional features, the soft tissue attachment region can be defined on a medial surface of a medial condyle of the femoral prosthesis and the soft tissue can be a medial collateral ligament (MCL). According to still another example, the soft tissue attachment region can be defined on an interior wall surface of the femoral prosthesis and the soft tissue can be either an anterior cruciate ligament (ACL) or posterior cruciate ligament (PCL).

A method for securing a soft tissue to a first prosthetic implant can include providing a first prosthetic component that defines a threaded bore at a soft tissue attachment region. A first construct formed of porous metal can be provided that defines a first aperture. A second construct can be provided that defines a second aperture. A soft tissue can be positioned between the first construct and the second construct. A fastener can be advanced through the second aperture and the first aperture. The fastener can be further advanced into the threaded bore such that the soft tissue is progressively captured between the first and second constructs.

The method according to additional features of the present application can include removing the fastener from the first prosthetic component. The first construct can be removed from the first prosthetic component. The first construct can have the soft tissue ingrown within the porous material. The first prosthetic component can be replaced with a second prosthetic component having a second soft tissue attachment region. The first construct with the soft tissue ingrown within the porous material can be located at the second soft tissue attachment region. A fastener can be advanced through the second aperture and the first aperture. The fastener can be further advanced into a second threaded bore defined on the second prosthetic component.

Further areas of applicability of the present disclosure will become apparent from the detailed description provided hereinafter. It should be understood that the detailed description and specific examples, while indicating the preferred embodi-

BRIEF DESCRIPTION OF THE DRAWINGS

The skilled artisan will understand that the drawings, described below, are for illustration purposes only. The drawings are not intended to limit the scope of the present teachings in any way:

FIG. 12 is an exploded side view of an exemplary attachment assembly wherein a first member is engaged in a recessed portion of an attachment surface of a proximal femoral prosthesis according to an example of the present teachings;

DETAILED DESCRIPTION OF VARIOUS EMBODIMENTS

The following description of the embodiment(s) is merely exemplary in nature and is in no way intended to limit the disclosure, its application, or uses. Moreover, while embodiments of the present teachings are discussed in detail below with regard to attaching soft tissue to proximal and distal femoral prosthesis, those skilled in the art will recognize the other types of soft tissue attachment to other joints such as, but not limited to: a hip in general, a knee in general, an elbow (proximal ulnar component, distal humerus component), a shoulder (proximal humerus component), or other areas of the body that may employ the present teachings.

Figure 1:
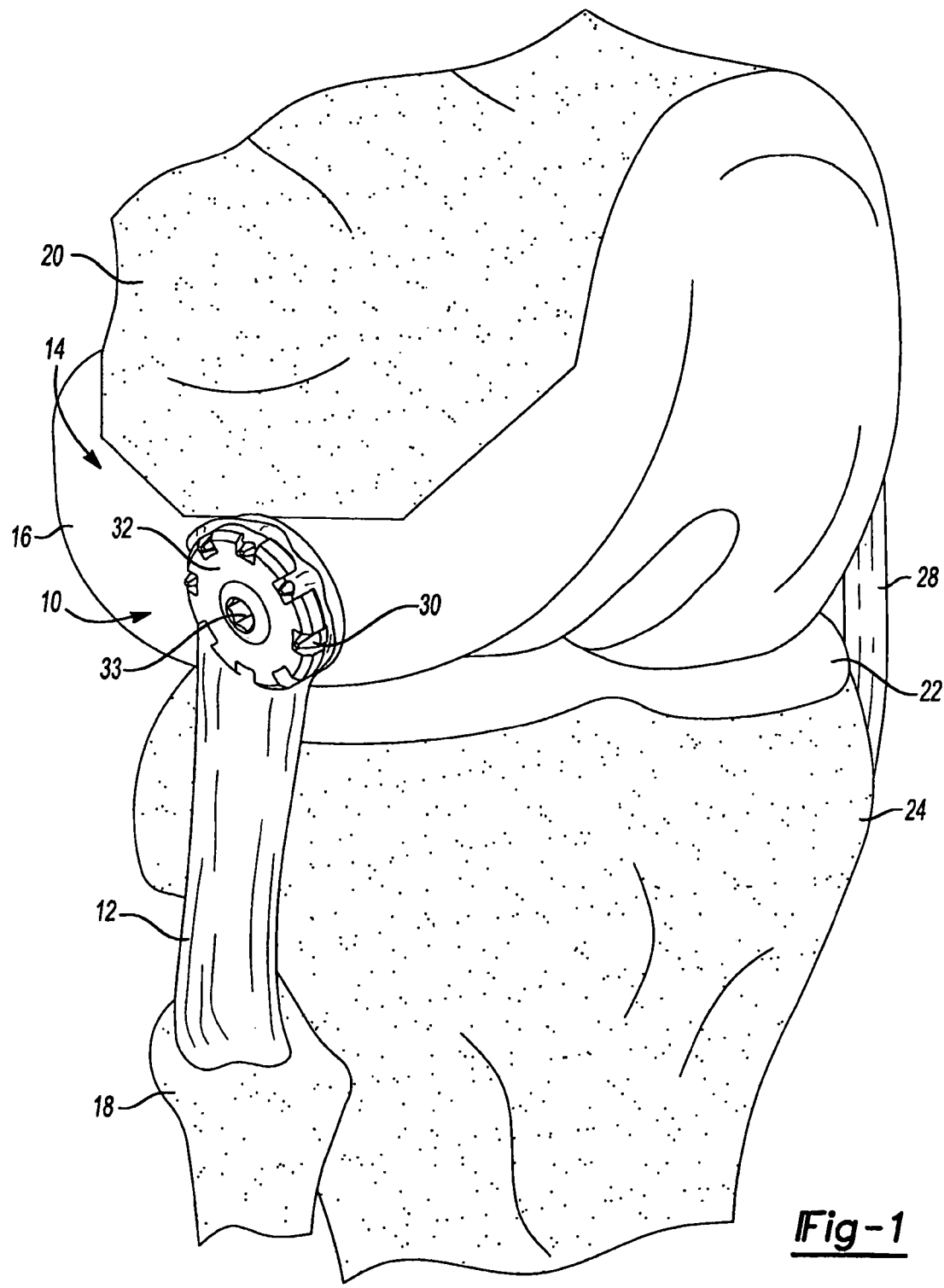
FIG. 1 is perspective anterior/lateral view of a right knee having a soft tissue securing assembly associated with a lateral collateral ligament (LCL) according to one example of the present teachings.
Figure 3:
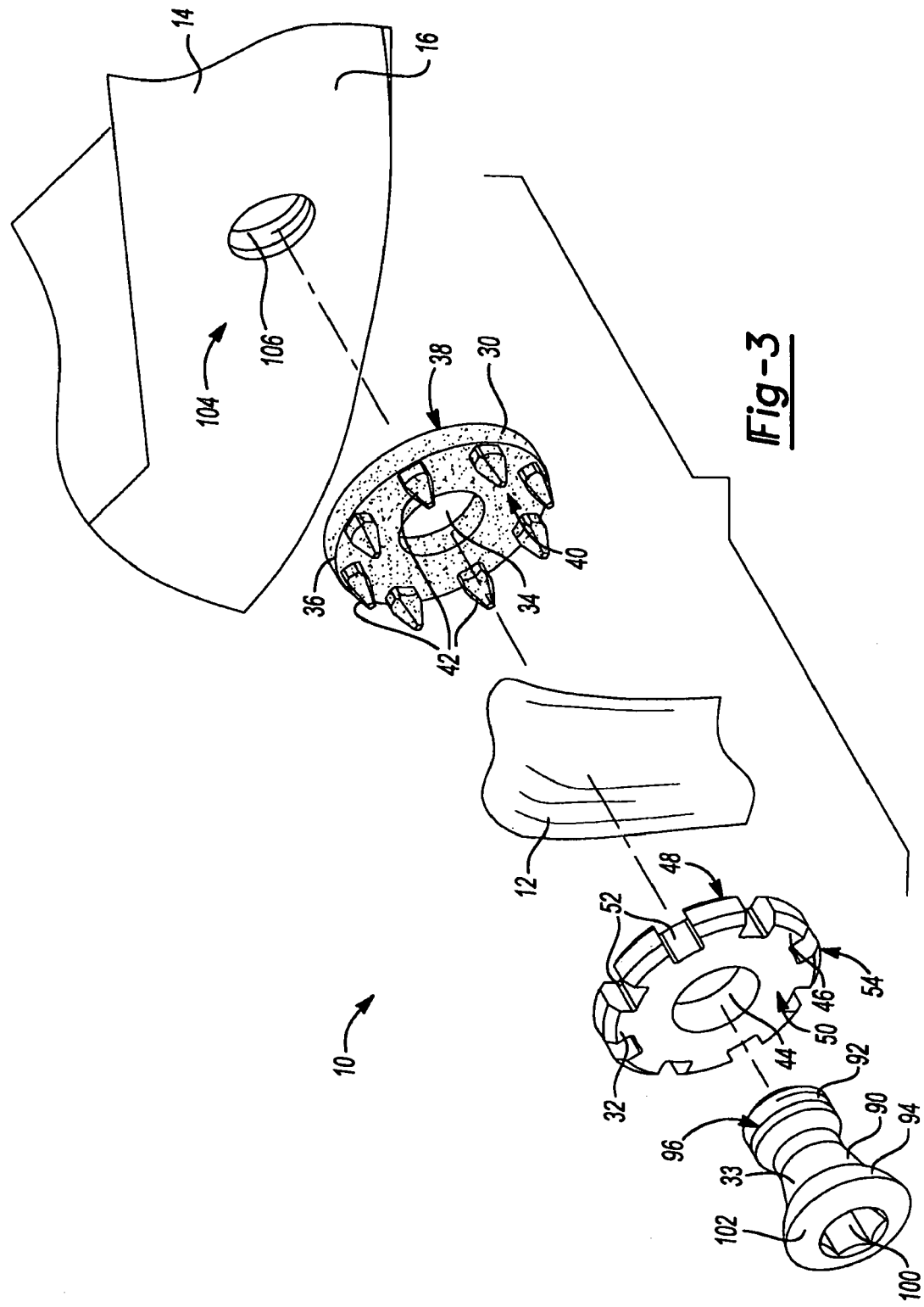
FIG. 3 is an exploded view of the soft tissue securing assembly of FIG. 1 and including an exemplary fastener, outboard washer and inboard washer.

With initial reference to FIGS. 1 and 3, a securing assembly 10 according to the present teachings is illustrated and shown operatively securing a soft tissue 12 to a prosthetic implant 14. In the particular example shown, the soft tissue 12 is a lateral collateral ligament (LCL) and the prosthetic implant 14 is a distal femoral prosthesis 16. The LCL is naturally secured on one end to a fibula 18 and on the other end to the distal femoral prosthesis 16 by way of the securing assembly 10. The distal femoral prosthesis 16 is shown implanted on a distal femur 20. A tibial component 22 can also be implanted onto a tibia 24. While not specifically shown, a similar securing assembly can be provided at the medial side of the distal femoral prosthesis 16 for securing a medial collateral ligament (MCL) 28.

The securing assembly 10 can generally define a first construct or washer 30, a second construct or washer 32 and a fastener 33. The first washer 30 can define a first aperture 34. In one example, the first aperture 34 can be a centrally defined through-hole. The first washer 30 can define a disk shaped body 36 having an inboard face 38 and an outboard face 40. A plurality of extension portions 42 can be defined around the outboard face 40 of the first washer 30. According to the example shown in FIG. 3, the extension portions 42 are in the form of spikes. The second washer 32 can define a second aperture 44. In one example, the second aperture 44 can be a centrally defined through-hole. The second washer 32 can define a disk shaped body 46 having an inboard face 48 and an outboard face 50. A plurality of notches 52 can be formed around a perimeter 54 of the second washer 32. In one example, the plurality of notches 52 can be configured to accept the plurality of extension portions 42 in an assembled position (FIG. 1).

Figure 2:
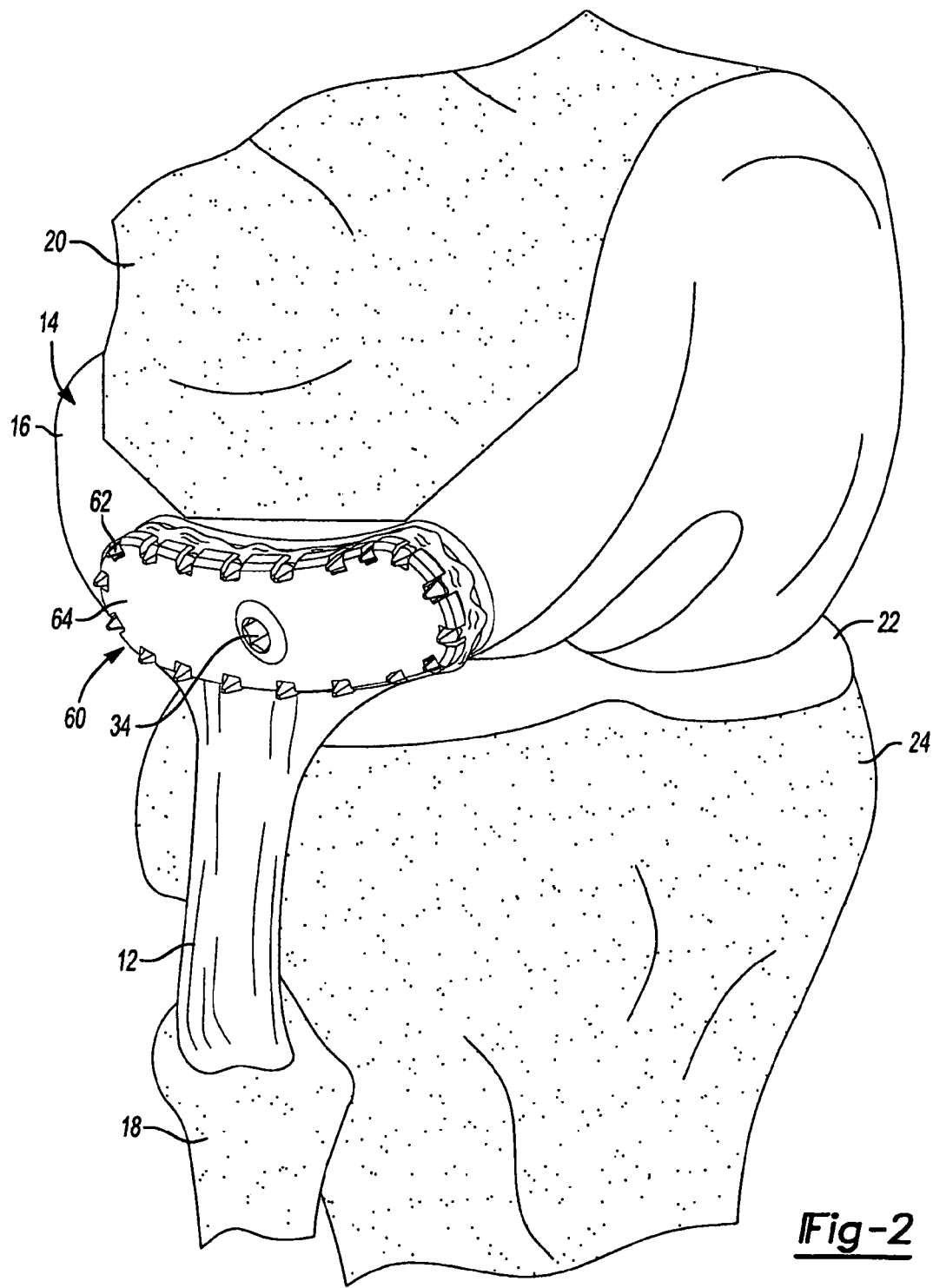
FIG. 2 is perspective anterior/lateral view of a right knee having a soft tissue securing assembly associated with a lateral collateral ligament (LCL) according to another example of the present teachings.
Figure 6:
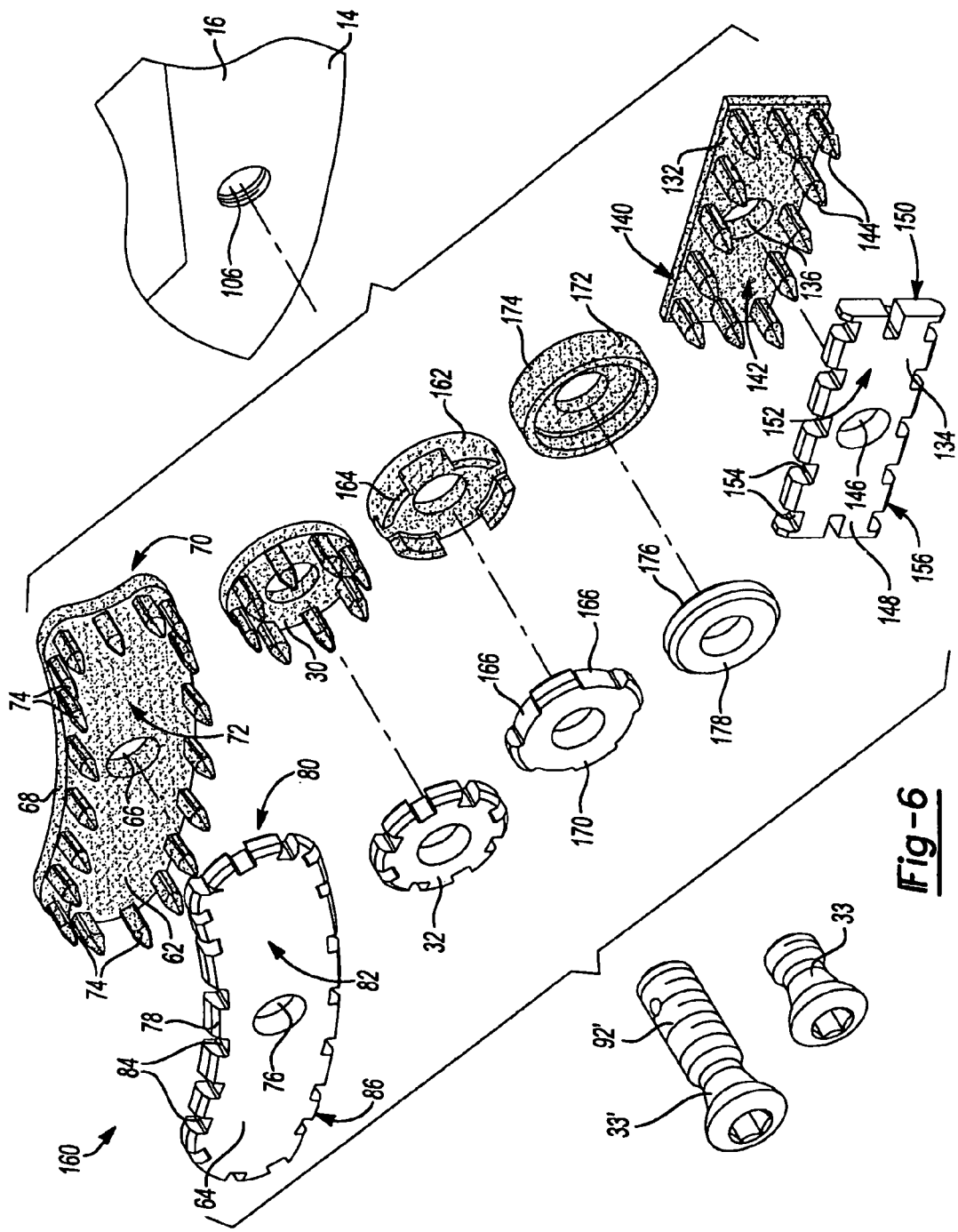
FIG. 6 is an exploded perspective view of exemplary securing assemblies according to the present teachings.

In the example shown in FIGS. 1 and 3, both of the first and second washers 30 and 32 define a body 36 and 46 that is substantially planar. As illustrated in FIG. 2, a securing assembly 60 with additional features, is shown having a generally arcuate profile as will be described in greater detail herein. The securing assembly 60 generally includes a first construct or plate 62, a second construct or plate 64 and a fastener 33. The first plate 62 can define a first aperture 66 (FIG. 6). In one example, the first aperture 66 can be a centrally defined through-hole. The first plate 62 can define a curved body 68 having an inboard face 70 and an outboard face 72. A plurality of extension portions 74 can be defined around the outboard face 72 of the first plate 62. According to the example shown in FIG. 2, the extension portions 74 are in the form of spikes. The second plate 64 can define a second aperture 76. In one example, the second aperture 76 can be a centrally defined through-hole. The second plate 64 can define an arcuate body 78 having an inboard face 80 and an outboard face 82. A plurality of notches 84 can be formed around a perimeter 86 of the second plate 64. In one example, the plurality of notches 84 can be configured to accept the plurality of extension portions 74 in an assembled position (FIG. 2).

In one example, the first construct 30, 62 can be formed of porous biocompatible material. The porous biocompatible material can include porous titanium. In general, the porous material used herein can provide pores that are irregular in size and orientation. Other suitable porous biocompatible materials can be found in co-owned and co-pending U.S. patent application Ser. No. 11/357,929, which is expressly incorporated by reference herein. The porous biocompatible material encourages tissue ingrowth of the soft tissue 12.

In one example, the second construct 32, 64 can be formed of solid biocompatible material such as titanium for example. According to additional features, the second construct 32, 64 can be alternately formed of porous biocompatible material. The porous biocompatible material can include porous titanium or other porous biocompatible materials referenced above.

Returning now to FIG. 3, the fastener 33 can define an intermediate portion 90 extending between a distal end 92 and a proximal end 94. The distal end 92 can define threads 96. The proximal end 94 can define a tool engagement feature 100. The tool engagement feature 100 can be any suitable tool engagement detail such as a hex-head for example. The proximal end 94 can further define a conical body portion 102. The conical body portion 102 can suitably nest within the second aperture 44 (or 76) of the second washer 32 (or plate 64). In this way, the proximal end 94 of the fastener 33 can rest substantially flush with the outboard surface 50 of the second washer 32 (or outboard face 82 of plate 64).

With continued reference to FIG. 3, the prosthetic implant 14 can define an attachment region 104 having a threaded bore 106 therein. The threaded bore 106 can be configured to threadably mate with the threads 96 at the distal end 92 of the fastener 33. In other examples, the attachment region 104 can be defined on the host bone and the fastener 33 can be a bone screw for securing the assembly onto the host bone.

Figure 4:
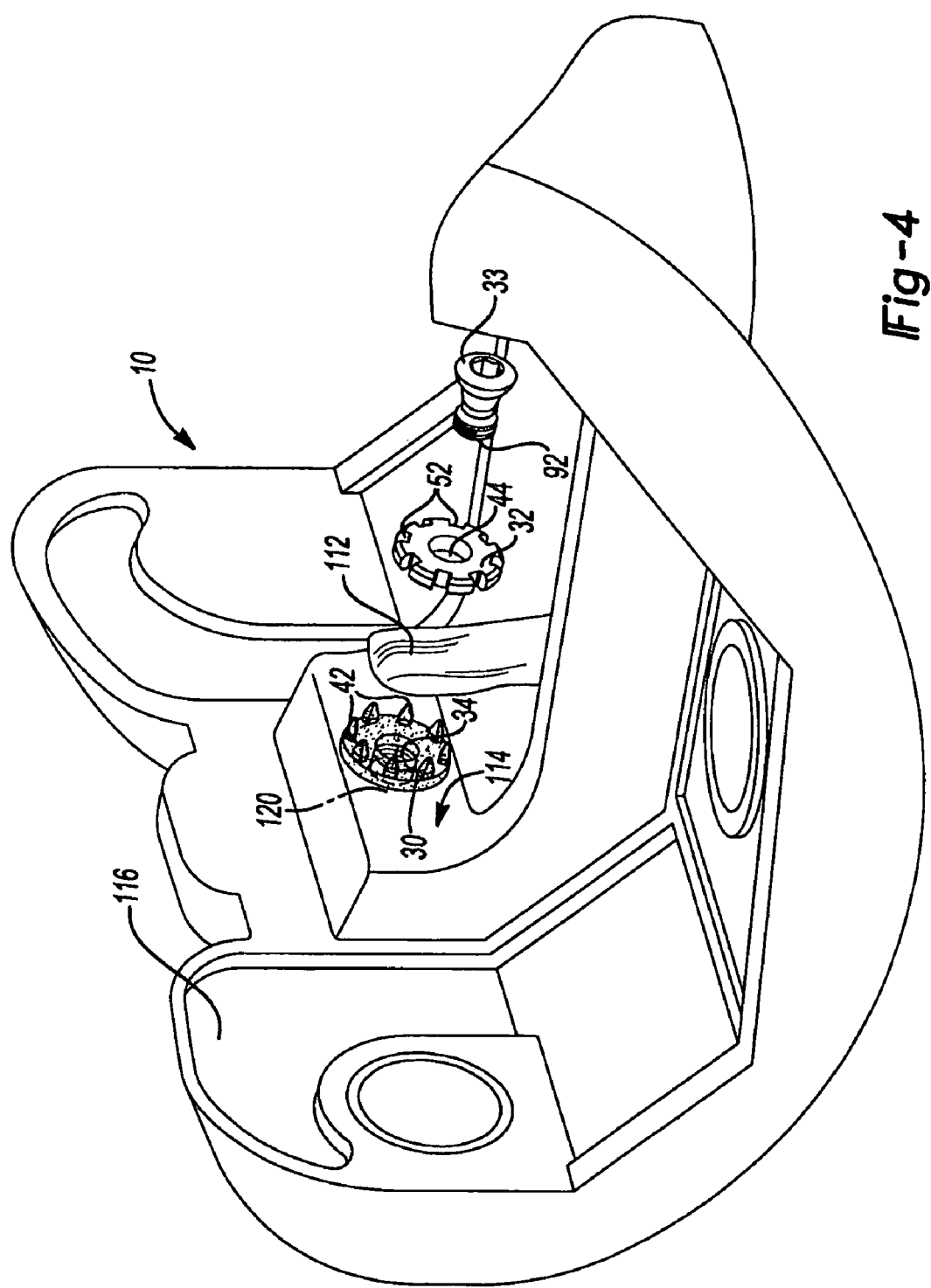
FIG. 4 is a posterior perspective view of a distal femoral prosthesis shown with an exemplary securing assembly in exploded view.

With reference now to FIG. 4, the securing assembly 10 is shown securing a posterior cruciate ligament (PCL) or an anterior cruciate ligament (ACL) 112 to an inboard wall 114 of a distal femoral prosthesis 116. The inboard wall 114 of the distal femoral prosthesis 116 can define a threaded bore 120 that threadably receives the distal end 92 of the fastener 33.

Figure 5:
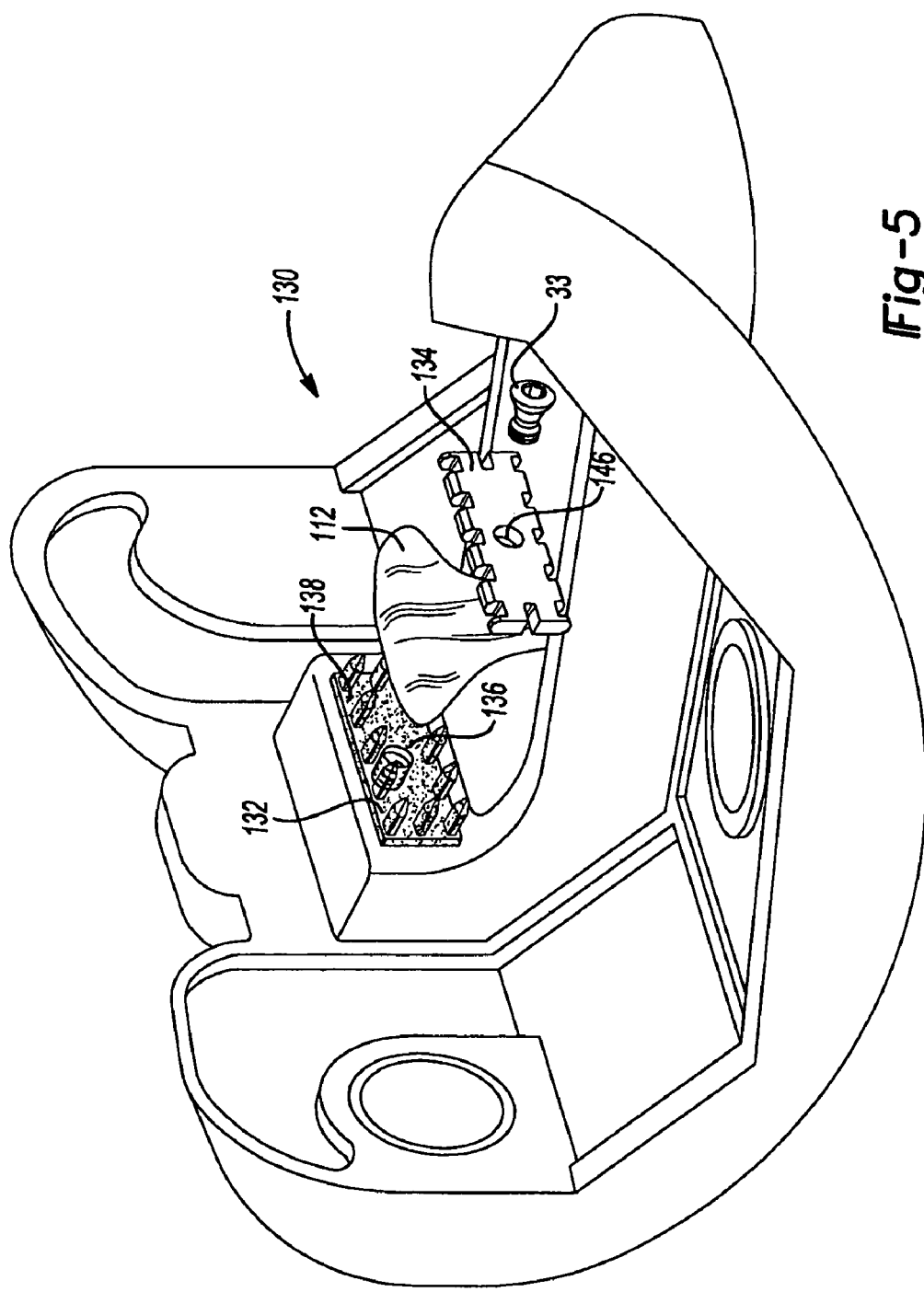
FIG. 5 is a posterior perspective view of a distal femoral prosthesis shown with another exemplary securing assembly in exploded view.

As illustrated in FIG. 5, a securing assembly 130 according to additional features is shown having a generally planar, rectangular profile as will be described in greater detail below. The securing assembly 130 can generally include a first construct or plate 132, a second construct or plate 134 and a fastener 33. The first plate 132 can define a first aperture 136. In one example, the first aperture 136 can be a centrally defined through-hole. The first plate 132 can define a planar body 138 having an inboard face 140 (FIG. 6) and an outboard face 142. A plurality of extension portions 144 can be defined around the outboard face 142 of the first plate 132. According to the example shown in FIG. 5, the extension portions 144 are in the form of spikes. The second plate 134 can define a second aperture 146. In one example, the second aperture 146 can be a centrally defined through-hole. The second plate 134 can define a planar body 148 having an inboard face 150 and an outboard face 152. A plurality of notches 154 can be formed around a perimeter 156 of the second plate 134. In one example, the plurality of notches 154 can be configured to accept the plurality of extension portions 144 in an assembled position (similar to that shown with the securing assembly 10 in FIG. 1).

With reference now to FIG. 6, a plurality of attachment assemblies 160 are shown. In addition to the first and second constructs described above, a first construct 162 can be provided having a plurality of raised walls 164. The raised walls 164 can be positioned within notches 166 defined around a second construct 170. A first construct 172 can define a continuous wall 174 that can surround a perimeter of a second construct 178. Another screw 32' can define a longer distal end 92'. As can be appreciated, a kit of attachment assemblies can be provided such that a surgeon can easily select a suitable prosthetic implant, first construct, second construct and fastener for a particular application.

An exemplary method of attaching soft tissue to a prosthetic implant 14 using one of the attachment assemblies 160 will now be described. At the outset, a surgeon can select a suitable first construct (30 etc.), second construct (32 etc.) and fastener (33 etc.) for a particular application. Concurrently, a surgeon can select a desired prosthetic implant 176, such as the distal femoral prosthesis 16, 116 provided herein. The first construct (30, etc.) can then be positioned adjacent to the attachment region 104 of the prosthetic implant 14. The soft tissue (12 etc.) can then be positioned intermediate of the outboard face (40 etc.) of the first construct (30 etc.) and the inboard face (48 etc) of the second construct (32 etc.). At this point, the extension portions (42 etc.) can be aligned with the notches (52 etc.). The fastener (33 etc.) can then be passed through the second aperture (44 etc.) of the second construct (32 etc.), pierced through the soft tissue (12 etc.), passed through the first aperture (34 etc.) of the first construct (30 etc.), and threaded into the threaded bore 106. As the fastener 33 is progressively threaded into the threaded bore 106, the extension portions (42 etc.) can pierce through the soft tissue (12 etc.) further capturing the soft tissue (12 etc.) between the first and second constructs (30 and 32 etc.).

Figure 7:
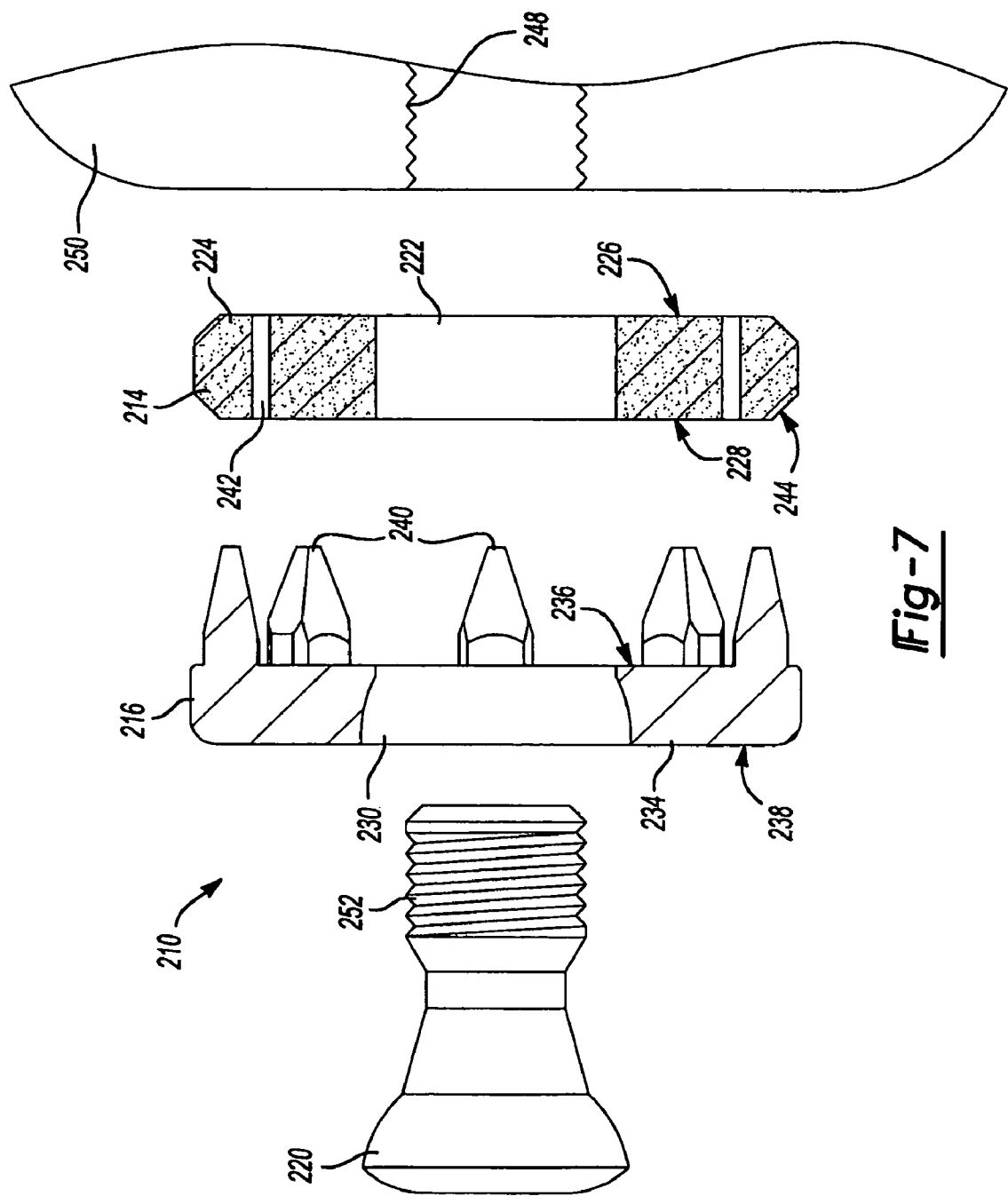
FIG. 7 is an exploded side view of an exemplary securing assembly wherein the fastener is configured to threadably mate with a threaded bore formed in the prosthesis component according to a first example.
Figure 8:
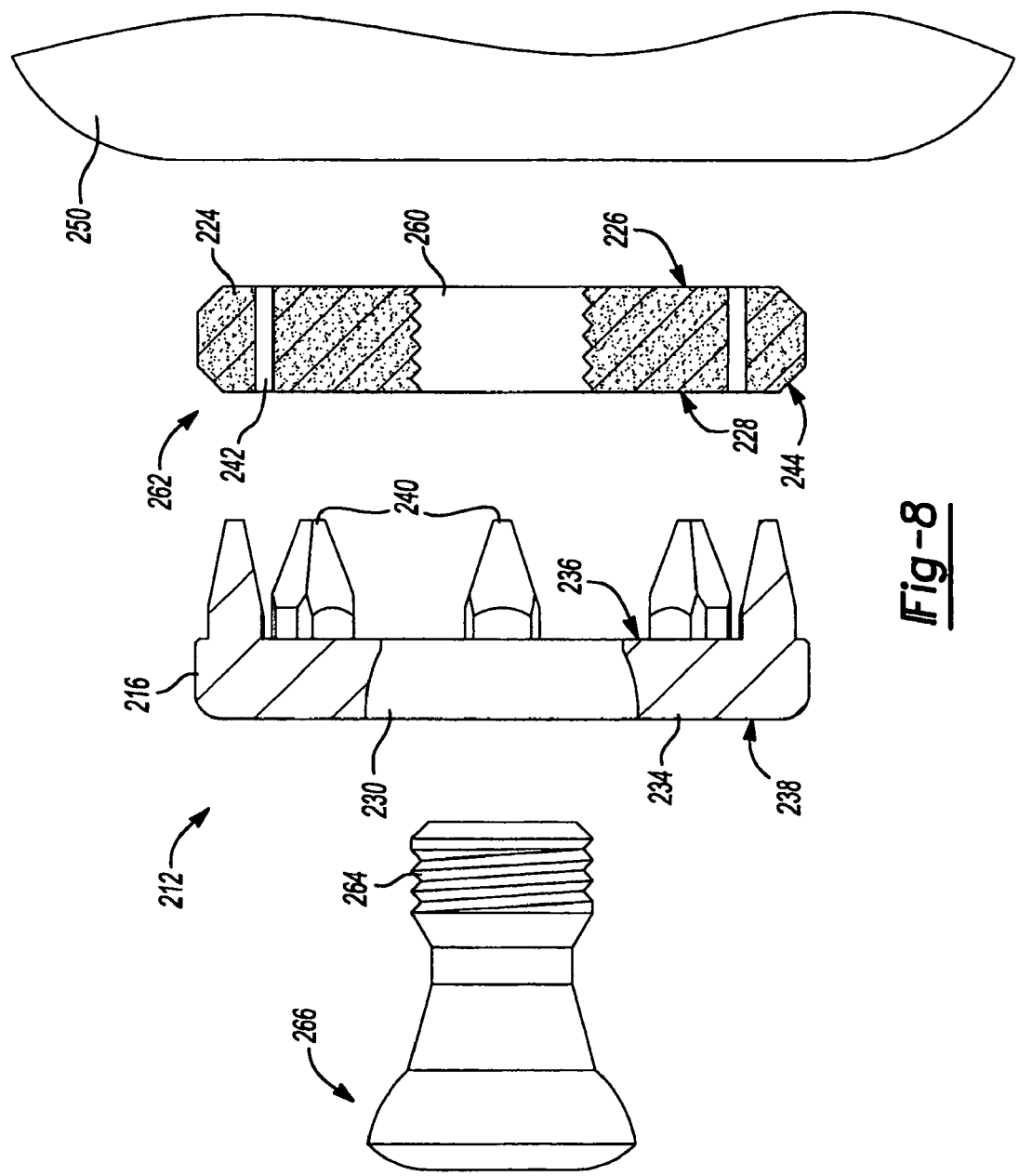
FIG. 8 is an exploded side view of an exemplary securing assembly wherein the fastener is configured to threadably mate with a threaded bore formed in the inboard washer according to a second example.

FIGS. 7 and 8 show securing assemblies 210 and 212 according to additional features. The securing assembly 210 generally includes a first construct or plate 214, a second construct or plate 216, and a fastener 220. The first plate 214 can define a first aperture 222. In one example, the first aperture 222 can be a centrally defined through-hole. The first plate 214 can define a planar body 224 formed of porous metal such as described herein. The first plate 214 can have an inboard face 226 and an outboard face 228. The second plate 216 can define a second aperture 230. In one example, the second aperture 230 can be a centrally defined through-hole. The second plate 216 can be formed of a solid metal or a porous metal as described herein. The second plate 216 can define a planar body 234 having an inboard face 236 and an outboard face 238. A plurality of extension portions 240 can be defined around the inboard face 236 of the second plate 216. According to the example shown in FIG. 7, the extension portions are in the form of spikes. A plurality of notches 242 can be formed around a perimeter 244 of the first plate 214. In one example, the plurality of notches 242 can be configured to accept the plurality of extension portions 240 in an assembled position. A threaded bore 248 can be defined in a prosthesis 250 for threadably receiving the distal end 252 of the fastener 220.

The securing assembly 212 shown in FIG. 8 is constructed substantially similar to the securing assembly shown in FIG. 7, except that a thread is provided or formed in a threaded aperture 260 of a first construct 262. The threaded aperture 260 is configured to threadably accept a distal end 264 of the fastener 266 in an assembled position. The inboard face 226 of the first construct 262 can be secured to the prosthesis 250 by an adhesive such as bone cement. Other methods may be used to secure the first construct 262 to the prosthesis 250.

Figure 9:
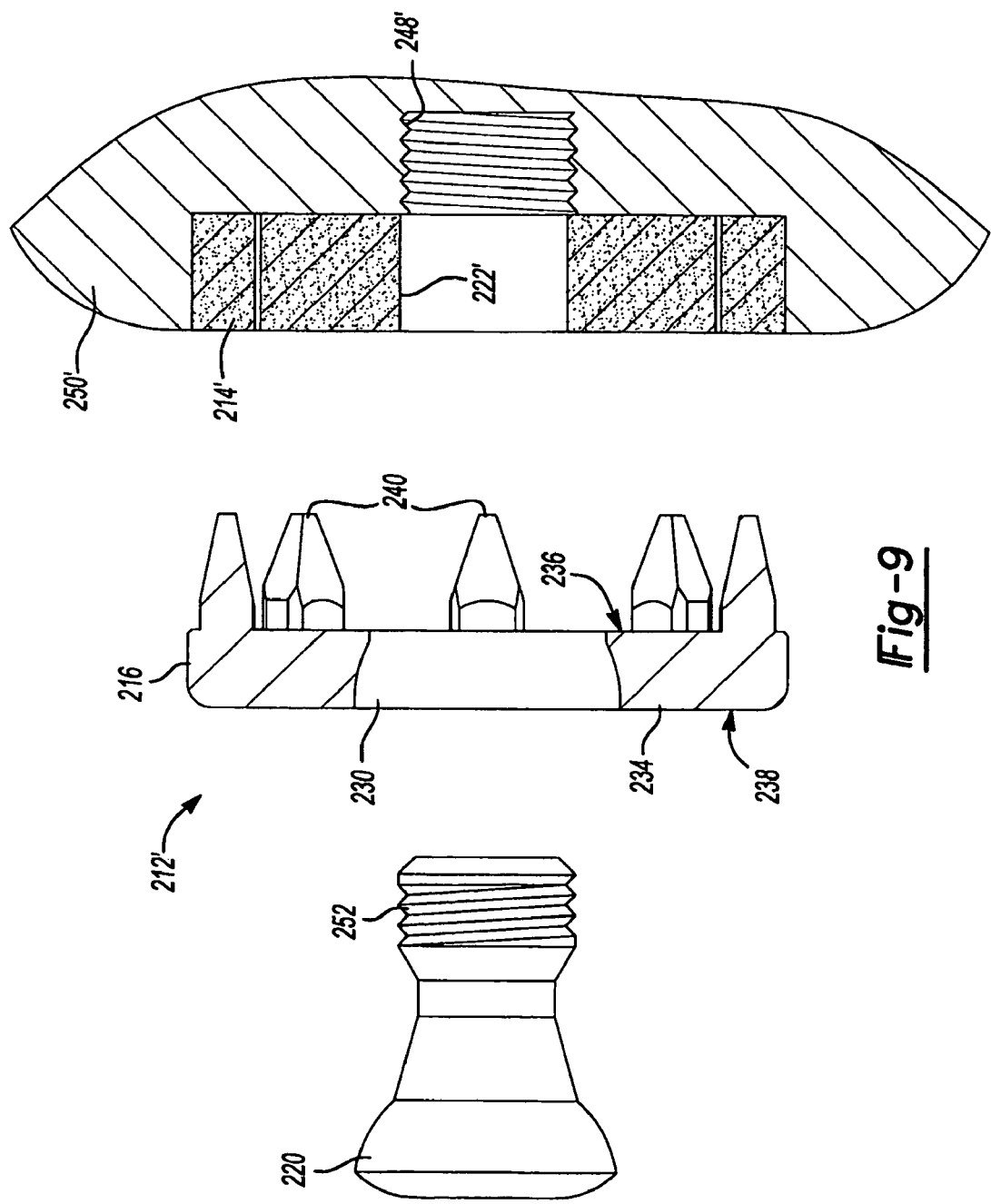
FIG. 9 is an exploded side view of an exemplary securing assembly wherein a porous metal portion is integrally formed in the prosthesis component according to one example.

FIG. 9 shows a securing assembly 212' according to additional features. The securing assembly 212' generally includes a first construct or plate 214', a second construct or plate 216, and a fastener 220. The first plate 214' can define an aperture 222'. In one example, the aperture 222' can be a centrally defined through-hole. The first plate 214', according to the example shown in FIG. 9, can be formed of porous metal, as described herein. Additionally the first plate 214' may be integrally formed with a prosthesis 250'. The prosthesis 250' can define a threaded bore 248' for threadably receiving the distal end 252 of the fastener 220.

Figure 10:
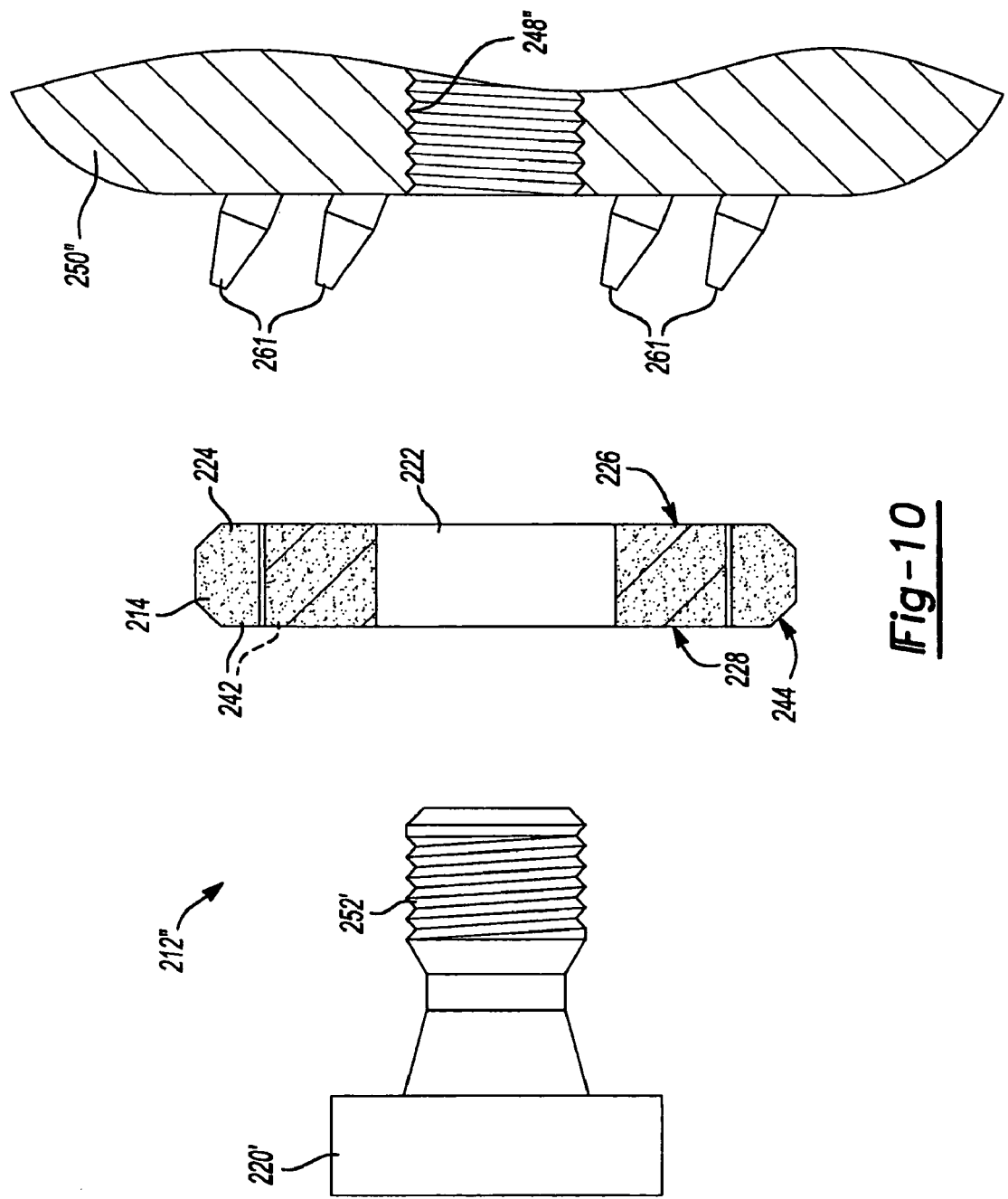
FIG. 10 is an exploded side view of an exemplary securing assembly wherein spikes are machined onto the prosthesis component according to one example.

FIG. 10 illustrates a securing assembly 212" according to additional features. The securing assembly 212" generally includes a prosthesis 250" having a threaded bore 248" for threadably receiving a distal end 252' of a fastener 220'. The prosthesis 250" can include one or more spikes 261 formed thereon. The spikes 261 can be integrally formed, such as by machining, with the prosthesis 250". In one example, the spikes 261 can extend at an angle generally greater than 90° (obtuse) and in a direction away from an originating point of the cruciate ligament 112. The spikes 261 can therefore pierce the cruciate ligament 112 at a favorable angle for capturing the ligament 112 at the prosthesis 250". In the example shown in FIG. 10, the need for a separate spiked washer can be eliminated.

According to one benefit of the instant disclosure, the soft tissue can have long term viability at the attachment region 104. The porous material of the first and/or the second construct (30 and 32 etc.) can facilitate substantial tissue ingrowth. In the event that the implant (i.e., the prosthetic implant 14) would need to be revised, the fastener (33 etc.) can be withdrawn from the threaded bore 106. The soft tissue (12 etc.) that has grown into the first construct (30 etc.) and second construct (32 etc.), can be collectively removed and or excised. A new prosthetic implant can then be implanted, and the first and second construct (30 and 32 etc.), with ingrown soft tissue (12 etc.), can be re-fastened to the replacement implant. Accordingly, the soft tissue engaging members can be completely separate from the remainder of the prosthesis and be removed from the prosthesis at a selected time and procedure. Although, according to various embodiments, at least one of two members of a connection portion can be substantially permanently connected to another portion of the prosthesis, it is generally for completely separately and later connected to another implantable portion of the prosthesis.

Figure 11A:
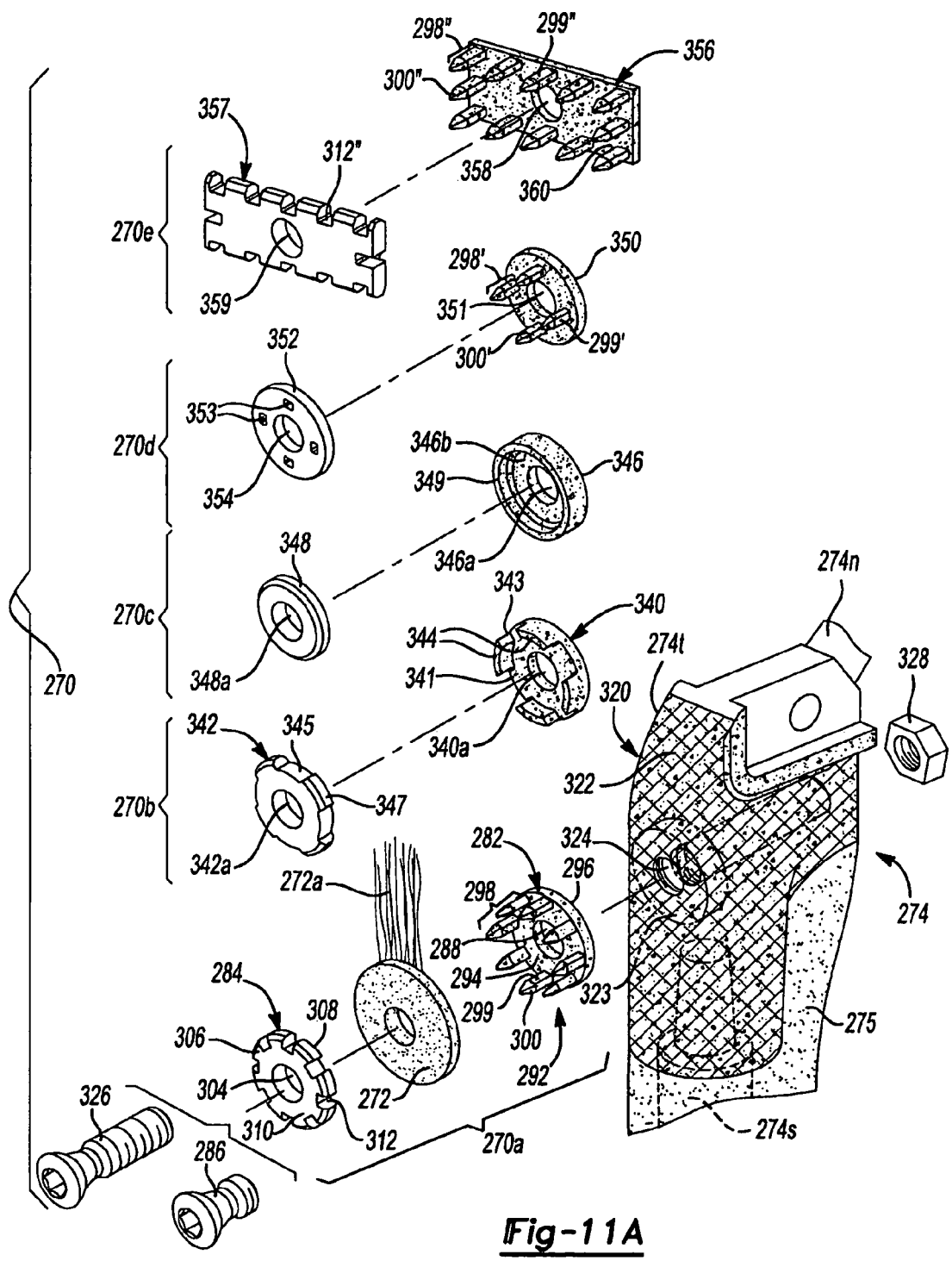
FIG. 11A is an exploded perspective view of a right proximal femoral prosthesis, attachment assemblies, and a tissue portion, according to various embodiments.
Figure 15A:
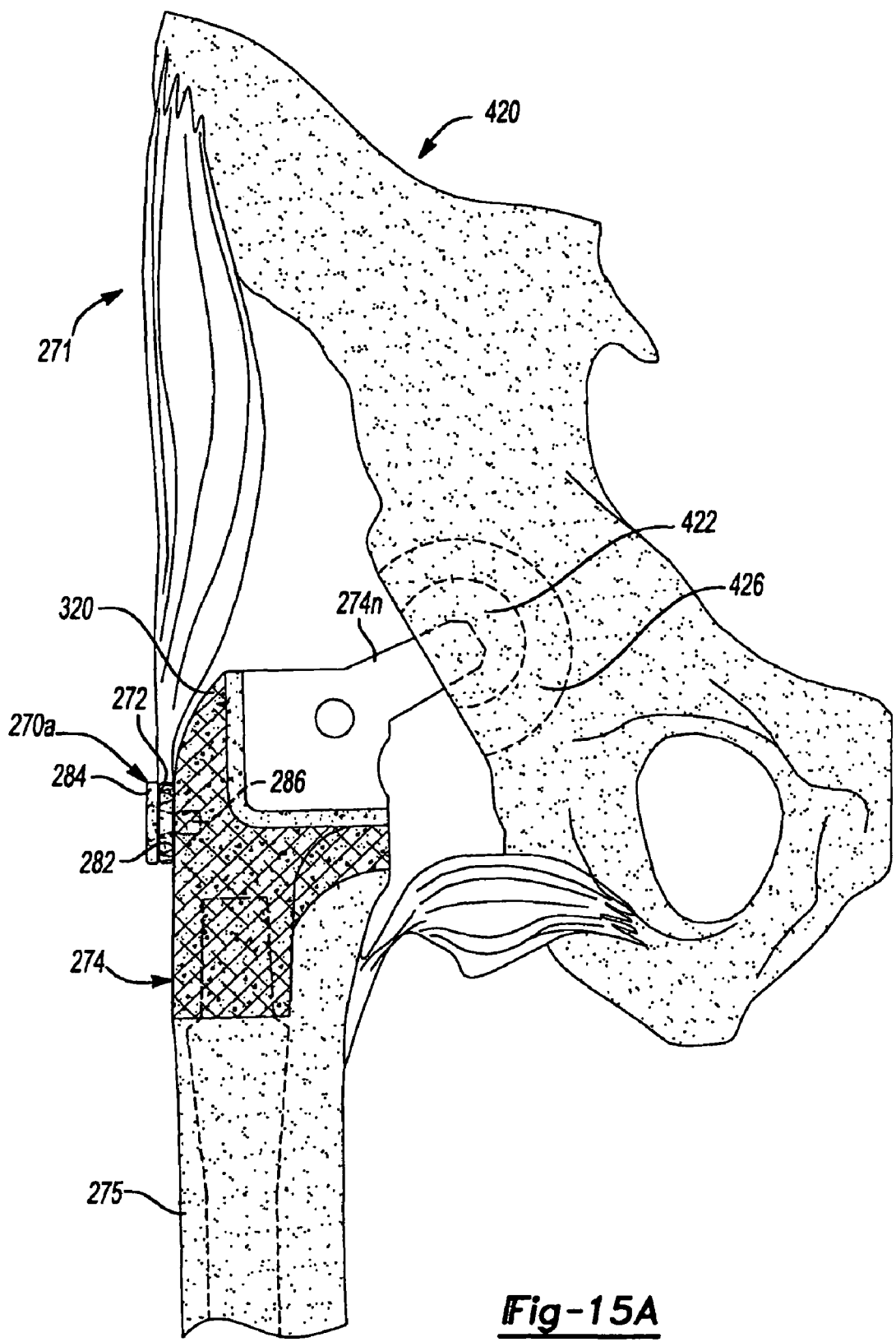
FIGS. 15A-15C are environmental anterior views of a hip including an exemplary attachment assembly and proximal femoral prosthesis, and exemplarily illustrating an implantation and revision procedure.

A prosthesis including the first and second construct, according to various embodiments, can be provided in any appropriate portion of the anatomy. For example, a proximal femoral prosthesis 274, as illustrated in FIG. 11A, can be provided to replace a portion of a femur 275. For example, the proximal femoral prosthesis 274 can include a trochanter or replacement portion 274t that includes an area for attachment or positioning a tissue portion 271 (FIG. 15A). The trochanter replacement portion 274t can be interconnected with a stem 274s that can extend into a selected portion of the anatomy, such as an intramedullary region of a femur. In addition, with reference to FIG. 15A, the tapered neck portion 274n can extend from the trochanter replacement portion 274t. The tapered neck portion 274n can engage a prosthetic femoral head 422 (FIG. 15A). After implantation, the prosthetic femoral head 422 can articulate with an implanted acetabular prosthesis 426 (FIG. 15A) or a natural acetabulum, according to various embodiments. Appropriate pieces, which can be used according to the disclosure herein, can include those sold with and for use with the Mallory-Head Modular Calcar Revision System™ sold by Biomet Orthopedics, Inc., having a place of business in Warsaw, Ind., United States of America.

The proximal femoral prosthesis 274 can define the tissue attachment region 320 having an attachment surface 322 defined on a lateral surface of the proximal femoral prosthesis 274. The attachment surface 322 can be further defined by a bore 324. The bore 324 can be threaded to accept a threaded fastener 286. The bore 324 can also be smooth to accept a second fastener assembly including a first fastener member 326 that threadably engages a second fastener member 328 on a medial surface of the proximal femoral prosthesis 274.

In continued reference to FIG. 11A, a plurality of attachment assemblies 270 can be connected with the proximal femoral prosthesis 274. The attachment assemblies 270 can be used to connect or place a tissue portion 271 relative to or near the proximal femoral prosthesis 274. The attachment assemblies, according to various embodiments, can be formed and provided completely separately from the prosthesis, such as the proximal femoral prosthesis 274. The attachment assembly 270 can include one or more members are that are also completely separate and removable from the proximal femoral prosthesis 274. This can allow ingrowth to be maintained with the attachment assemblies and the attachment assembly 270 can be removed as a single assembly from the proximal femoral prosthesis 274. It will be understood, however, according to various embodiments, that at least one of the members of the attachment assembly 270 can be substantially permanently connected to the proximal femoral prosthesis 274.

The tissue portion 271 can be a soft tissue portion 272a that is naturally attached to the greater trochanter of the femoral and is removed for implantation of the prosthesis 274. The tissue 271 can also include a bone portion 272 that is directly engaged with the attachment assemblies 270 that extend from a soft tissue 272a that is further attached to a portion of a pelvis 420. A tissue portion 271 can generally include a tendon of the abductors, for example, a tendon of the gluteus medius and minimus muscles. The tissue 271, including the tendon of these muscles, can be removed during a procedure and can be attached to the proximal femoral prosthesis 274 at the tissue attachment portion 320 during a selected portion of the implantation of the proximal femoral prosthesis 274.

According to various embodiments, the attachment assemblies 270 can include a first assembly 270a that has a first member 282, a second member 284, and a fastener 286. The first member 282 can define a first aperture 288. In one example, the first aperture 288 can be a centrally defined through-hole. The first member 282 can define a disk-shaped body 292 having an outboard face 294 and an inboard face 296, wherein the outboard face 294 engages the bone portion 272 and the inboard face 296 engages the proximal femoral prosthesis 274. Additionally, a plurality of projections 298 can be defined around the perimeter of the outboard face 294 of the first member 282.

According to one example, the projections 298 are in the form of spikes. The projections 298 can include a first extension portion 299 that can be substantially columnar or otherwise include a straightedge portion. The first extension portion 299 can then terminate in a tapered or pointed tip 300. The tapered or pointed tip 300 can allow for piercing of a selected material, such as the bone segment 272. The first extension portion 299 can then engage, substantially in a permanent or non-cutting manner, the bone portion 272. In this way, as discussed further herein, the first member 282 can assist in holding the bone member 272 at a selected location.

The second member 284 can define a second aperture 304. In one example, the second aperture 304 can be a centrally defined through-hole. The second member 284 can define a disk-shaped body 306 having an inboard face 308 and an outboard face 310, wherein the inboard face 308 engages the bone portion 272 and the outboard face 310 engages the fastener 286. A plurality of notches 312 can be formed around a perimeter of the second member 284.

In one example, the plurality of notches 312 can be configured to cooperate with the plurality of extensions 298 in a coupled position. The notches 312 can include a sidewall that defines the notches 312 that can be substantially complementary to the first extension portion 299 of the extensions 298. As the tapered portion 300 extends through the bone portion 272 and the notch 312, the first extension portion 299 can hold or engage the bone portion 272 and/or the notches 312.

The first member 282 and the second member 284 can engage and be positioned on two sides of the bone portion 272 to form a unit. The first fastener 286 or the second fastener assembly 326 can then be used to connect the unit to the proximal femoral prosthesis 274. As discussed herein, the unit can then be removed from the proximal femoral prosthesis 274 while maintaining substantially all of a boney ingrowth.

The first member 282 can be formed of porous biocompatible material. The second member 284 can be formed of solid biocompatible material, such as titanium. According to additional features, the second member 284 can be also or alternatively formed of porous biocompatible material. Therefore, both the first member 282 and the second member 284 can be formed of a biocompatible porous material. The porous material can allow for boney ingrowth of the bone portion 272 into the porous portion of the attachment assemblies 270. The porous material, as discussed herein, can allow for bone ingrowth substantially completely through either of the first member 282 or the second member 284. This can allow for substantial fixation of the bone portion 272 of the soft tissue after implantation of the proximal femoral prosthesis 274.

The porous material used to form the first and second members 282, 284 can be a substantially completely porous material. In other words, the porous material can include porosity that can extend through the material or member. This porosity can allow for a deep ingrowth of bone, as discussed herein. Appropriate materials include REGENEREX™ sold by Biomet, Inc., having a place of business in Warsaw, Ind., United States of America. Appropriate materials are also disclosed in U.S. patent application Ser. No. 11/357,929, filed Feb. 17, 2006, incorporated herein by reference. REGENEREX™ porous material or the material disclosed in the U.S. patent application Ser. No. 11/357,929 can allow for substantially complete boney ingrowth through a porosity that extends substantially through the porous material. For example, ingrowth may extend from a first side to a second side of a member formed from the porous material. A completely or through porosity through a material can allow a second material to extend or move completely through the porous material, such as from a first side to a second side, via the pores. Accordingly, the amount of ingrowth can allow for a substantial and strong hold of the bone portion 272 relative to the proximal femoral prosthesis 274.

With continuing reference to FIG. 11A, an attachment assembly 270b, according to various embodiments, is illustrated. The attachment assembly 270b includes a first member 340 and a second member 342. The first member 340 can include one or more walls 344 that extend from a surface of the first member 340, such as an outboard face or surface 341. The wall 344 can be positioned substantially along a perimeter or around a perimeter of the first member 340. The wall can be segmented with a depression or opening 343 provided between wall segments 344 to allow for the formation of the plurality of wall segments of the wall 344. A bore 340a can also be provided through the first member 340.

The second member 342 can define one or more depressions 345 between wall or projection portions 347 substantially at an exterior perimeter of the second member 342. The depressions 345 can cooperate with the walls 344 to allow for an appropriate mating or cooperation of the first member 340 and the second member 342. The cooperation of the walls 344 with the depressions 345 can assist in engaging the soft tissue 272a or the bone portion 272 of the tissue portion 271. For example, the wall 344 can extend through or around the bone portion 272 and be positioned within depressions 345 of the second member 342. A bore 342a can be provided through the second member 342. In addition, the first member 340 and the second member 342 can be formed of substantially solid materials or be formed of porous materials, including those discussed above.

An attachment assembly 270c including a first member 346 and a second member 348 is also illustrated in FIG. 11A. The first member 346 can include a substantially continuous wall 349 extending from a surface of the first member 346. The wall 349 can extend from an inboard face 346b of the first member 346. The continuous wall 349 of the first member 346 can be formed to substantially surround the second member 348 when the second member 348 is positioned relative to the first member 346. The bone portion 272 can also be formed to fit substantially within the continuous wall 349 of the first member 346. The second member 348 can then act as a washer and can be compressed against the bone portion 272 with the fastener members 286, 326. The soft tissue portion 272a, however, can be provided to extend around the wall 349 or through a clearance portion. Both the first member 346 and the second member 348 can be formed of non-porous materials, porous coated materials, or porous materials, including those discussed above. Also, the first member 346 can define a bore 346a and the second member 348 can define a bore 348a. Both bores 346a, 348a can pass through the respective first member 346 or second member 348.

According to various embodiments, an attachment assembly 270d can include a first member 350 and a second member 352. The first member 352 can include an aperture or throughbore 351 and the second member 352 can also define a bore 354. The first member 350 can also include projections 298'. The projections 298' can be substantially similar to the projections 298 of the attachment assembly 270a. Accordingly, the projection portion 298' can include a tapered region 300' and a first extension portion 299' can be a substantially columnar or straight side portion. In addition, the projections 298, 298' can be formed to extend at an appropriate angle from the respective members 282, 350. The angle can be about 90 degrees.

The projections 298' can engage or pass through the bone portion 272 similar to the projection 298 discussed in relation to the attachment assembly 270a. The projection 298 can further engage a passage 353 defined by the second member 352. The passage 353 can include a geometry or internal perimeter substantially similar to the perimeter of the projection 298'. Accordingly, the projection 298' can extend to or through the bone portion 272 or any portion of the tissue portion 271 and further engage or cooperate with a second member 352. Also, the second member 352 can include a throughbore or passage 354 that can allow the fastener assembly 286 and fastener assembly member 326 to pass through.

According to various embodiments, an attachment assembly 270e is further illustrated in FIG. 11A. The attachment assembly 270e can include a first member 356 and a second member 357. The first member 356 can include a throughbore or passage 358 and the second member 357 can include a second throughbore or passage 359. The first member 356 and the second member 357 can include substantially rectangular or square perimeters. The perimeters of the first member 356 and the second member 357, however, can be substantially complementary. The two members 356, 357 can cooperate or mate appropriately, as discussed herein, to engage the tissue portion 271.

The attachment assembly 270e can further include a projection or extension portion 298" to extend from an outboard or selected surface 360 of the first member 356. The projection 298" can be similar to the projection 298 of the attachment assembly 270a. Accordingly, the projection 298" can include a tapered portion 300" and a first extension portion 299". The first extension portion 299" can be a substantially columnar or flat portion. The second member 357 can include depressions or notches 312" similar to the notches 312 of the attachment assembly 270a. The notches 312" can cooperate with the projections 298" to hold the tissue portion 271 relative to the first member 356 and a second member 357. As discussed above, the fastener members 286, 326 can be positioned through the apertures 358, 359 to assist in holding the two members 356, 357 together and engage the proximal femoral prosthesis 274.

In addition, the first member 356 and the second member 357 can be formed of any appropriate materials. Appropriate materials can include non-porous materials, or porous materials, including those discussed above. In addition, as discussed above, the fully porous material can allow for ingrowths of bone substantially through a thickness of the members 356, 357 of the attachment assembly 270e.

It will be further understood that the attachment, such as assemblies 270a-270e can be provided with any appropriate geometry. The attachment assemblies 270a-270e, however, can generally provide two members to be positioned relative to the proximal femoral prosthesis 274 for interconnection of the tissue portion 271 relative to the proximal femoral prosthesis 274. These exemplary attachment assemblies 270a-270e can be used to interconnect with the tissue 271.

Figure 11B:
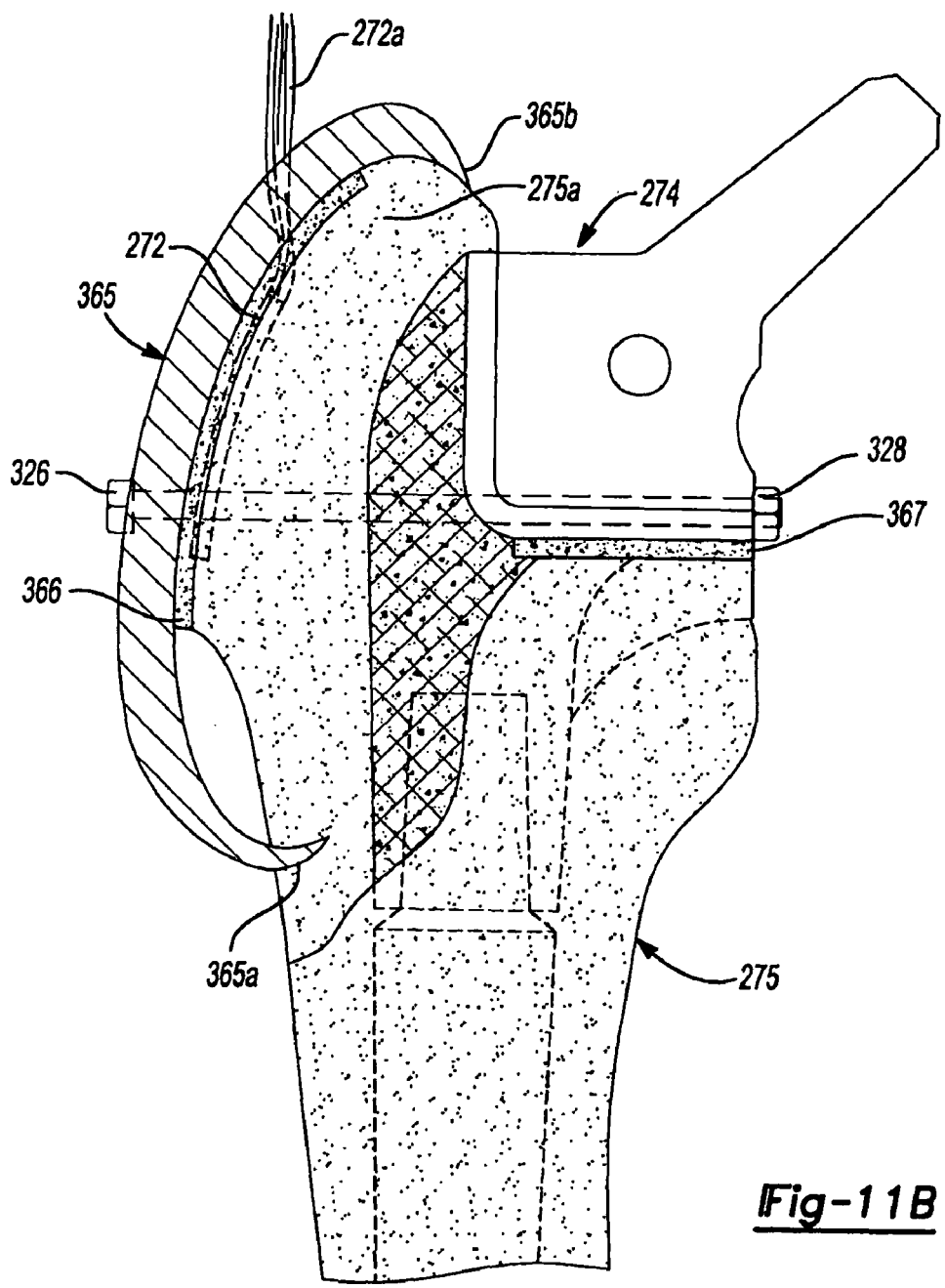
FIG. 11B is an environment assembled view of a right proximal femoral prosthesis, an attachment assembly, and a tissue portion, according to various embodiments.

The proximal femoral prosthesis 274 can be positioned within the femur 275 which has retained at least a portion of the greater trochanter 275a, as illustrated in FIG. 11B. When the portion of the greater trochanter 275a can be maintained, an attachment assembly 365 can be provided. It will be understood, however, that an attachment assembly according to any embodiment, including assemblies 270a-270e, can engage the greater trochanter 275a. The attachment assembly 365 can include a first end 365a and a second end 365b to substantially contact, such as with piercing or point contact, portions of the bone or the femur 275. The attachment assembly 365 can further include the first fastener member 326 that can pass through a passage or throughbore through the proximal femoral prosthesis 274 and engage a second fastener member 328 to hold the attachment assembly 365 relative to the proximal femoral prosthesis 274.

The attachment assembly 365 can be similar to the attachment assembly of the Mallory Head™ Modular Calcar Revision System. The attachment assembly 365, however, can include a portion of substantially porous material 366. The porous pad 366 can be positioned to contact a greater trochanter 275a of the femur 275. In addition, the tissue portion 272a, including the bone portion 272, can also be positioned between the porous pad 366 and the greater trochanter 275a. As discussed above, the porous material of the porous pad 366 allows for ingrowth of bone into the porous pad 366 for fixation of the tissue portion 271 relative to the proximal femoral prosthesis 274 or the femur 275. Also, the greater trochanter 275a can grow directly into the pad 366 whether or not the bone portion 272 is positioned next to the porous pad 366.

It will be understood that porous pads can also be provided relative to other areas. For example, a second porous pad 367 can be provided on a portion of the proximal femoral prosthesis 274. The porous pad 367 can allow for boney ingrowth and adhesion of the proximal femoral prosthesis 274 relative to a selected portion of the femur 275. Accordingly, it will be understood that the porous pad 367 can also or additionally be positioned on a lateral portion of the femoral stem 274, or any other appropriate location. As discussed above, the porous pad 366, 367 can be formed of the REGENEREX™ porous material sold by Biomet, Inc. According, a substantially porous material can allow for boney ingrowth substantially throughout the porous pads 366, 367.

According to various embodiments, the attachment region 320 can be defined by or include a recessed portion 323 operable to accept or cooperate with the first member 282, as illustrated in FIGS. 11A and 12. The outboard face 294 of the first member 282 sits flush with the attachment surface 322 of the proximal femoral prosthesis 274 in a coupled position. The depression 323 in the proximal femoral prosthesis 274 allows for a selected portion of the attachment assemblies 270a-270e to be positioned below an exterior surface of the proximal femoral prosthesis 274. This allows the attachment assemblies 270a-270e to be positioned in a manner to allow a surface of the attachment assembly to be flush with a surface of the proximal femoral prosthesis 274.

For example, the first member 282 of the attachment assembly 270a can be positioned within the depression 323. The projection 298 can be provided to substantially extend from the surface of the tissue attachment region 320. That is, the thickness of the first member 282 can be substantially equal to the depth of the depression 323.

In addition, positioning a portion of the attachment assemblies 270a-270e within the depression 323, such as the first member 282, can increase the holding or retention power of the attachment assemblies 270a-270e. The portion of the attachment assemblies maintained within the depression 323 can allow for additional surfaces of contact with the prosthesis 274 other than the fastener members 286, 326. Accordingly, the attachment assemblies 270a-270e can be held firmly and fixedly relative to the proximal femoral prosthesis 274. In addition, the depression 323 can be provided in any appropriate geometry to substantially match the geometry or complement the geometry of the attachment assembly portion being positioned within the depression 323.

The attachment assemblies 270a-270e can be provided substantially separate from the proximal femoral prosthesis 274. Accordingly, the attachment assemblies 270a-270e can be interconnected with the tissue portion 271, including the bone portion 272, and removed from the proximal femoral prosthesis 274 at a selected time. As discussed further herein, in FIGS. 15A-15C, the attachment assembly, such as the attachment assembly 270a, can be connected to the bone 272 at a selected time. During a later revision procedure, the attachment assembly connected to the bone portion 272 can be removed as a complete unit from the proximal femoral prosthesis 274 as the proximal femoral prosthesis 274 is removed. A new or revision proximal femoral prosthesis 274' can then be positioned within the femur 275 and the unit of the attachment assembly and the bone portion 272 can be reconnected to the revision proximal femoral prosthesis 274' without substantially disrupting or disconnecting any boney ingrowth into the attachment assembly 270a-270e. Accordingly, as discussed in further detail herein, the attachment assemblies 270a-270e can allow for a selected bone ingrowth over a period of time and can maintain the bone ingrowth or substantially maintain the bone ingrowth during a revision procedure where the attachment assembly 270a-270e and the bone portion 272 can be reconnected to a revision or different proximal femoral prosthesis.

Figure 13:
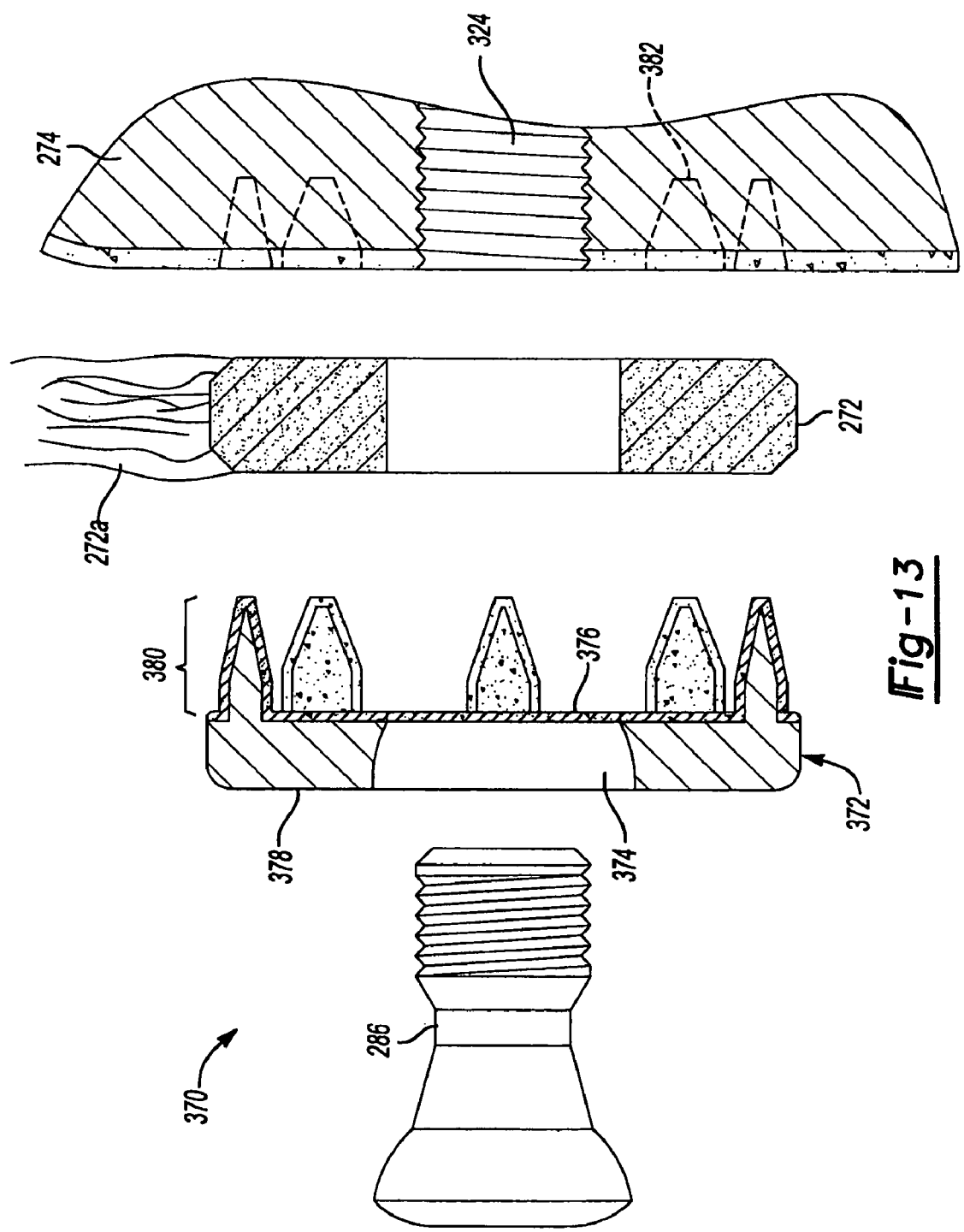
FIG. 13 is an exploded side view of a proximal femoral prosthesis and an exemplary attachment assembly including a first member, wherein the first member defines a plurality of extension portions.

FIG. 13 shows an attachment assembly 370 according to additional features. The attachment assembly 370 generally includes a first member 372, the fastener 286, and the proximal femoral prosthesis 274. The first member 372 can define a first aperture 374. In one example, the first aperture 374 can be a centrally defined through-hole. The first member 372 can have an inboard face 376 and an outboard face 378 wherein the inboard face 376 engages the bone portion 272 having soft tissue 272a thereon and the outboard face 378 engages the fastener 286.

A plurality of extension portions or projections 380 can extend from the inboard face 376 of the first member 372. The extensions 380 can be positioned near an external perimeter of the inboard face 376. The extension portions 380 can engage the bone portion 272 in any appropriate manner. For example, the bone portion 272 can be formed or augmented to include throughbores to allow the extension portion 380 to pass therethrough. Alternatively, the extension portions 380 can be pushed through the bone portion 272 such that the extension portions 380 are self driving, or form passages within the bone portion 272. The extension portion 380 can be formed to include a tapered portion such as the tapered portion 300 discussed above. Accordingly, the extension portion 380 can push through or into the bone portion 272.

In addition, the extension portion 380 can be provided in any appropriate height. For example, the height of the extension portion 380 can be substantially equivalent to a thickness of the bone portion 272. It will be understood, however, that the proximal femoral prosthesis 274 can also include recesses 382 to receive each of the projections 380. It will be further understood that the proximal femoral prosthesis 274 can also define the recess 323 which can substantially allow the bone portion, the extension portions 380, and the first member 372 to be positioned completely within the recess 323 in the proximal femoral prosthesis 274. According to various embodiments, selected portions of the bone portion 272 and the first member 372 can be positioned within the recess to increase or assist in fixing the tissue portion 271 to the proximal femoral prosthesis 274.

In one example, the inboard face 376 of the first member 372 can be coated or formed of porous biocompatible material, such as those discussed above. The outboard face 378 of the first member 372 can also be formed of solid biocompatible material, such as titanium. The fastener 286 can be threaded to engage a threaded bore 324. In another example, the bore 324 can be smooth to accept a fastener assembly including the first fastener member 326 that threadably engages the second fastener member 328 on the medial surface of the proximal femoral prosthesis 274.

Figure 14:
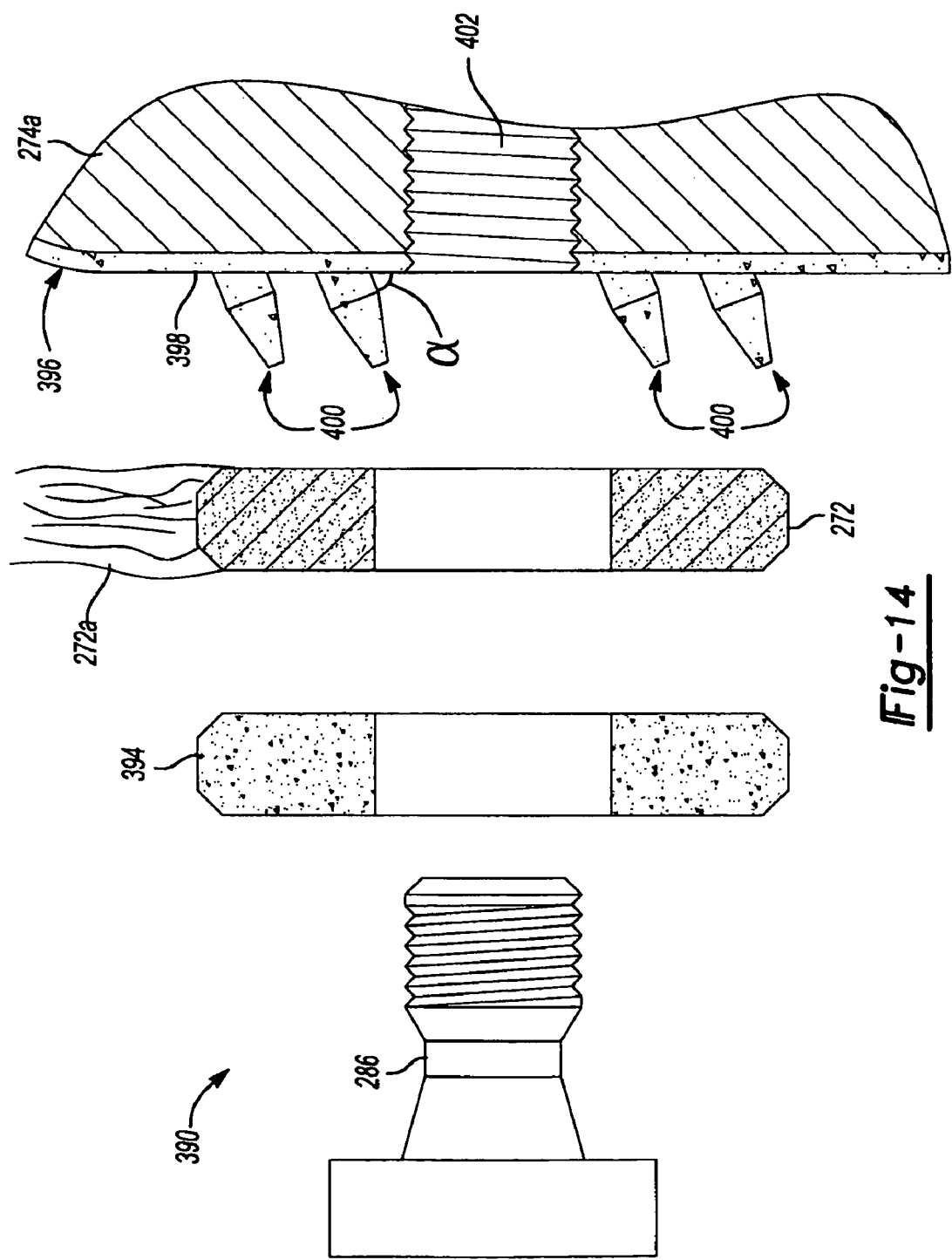
FIG. 14 is an exploded side view of an exemplary attachment assembly wherein spikes extend from a proximal femoral prosthesis according to one example.

FIG. 14 illustrates an attachment assembly 390 according to additional features. The attachment assembly 390 generally includes a proximal femoral prosthesis 274a, a first member or plate 394, the fastener 286, and an attachment region 396. The attachment region 396 can include an attachment surface 398 from which spikes 400 can extend. The spikes 400 can be integrally formed, such as by machining, with the proximal femoral prosthesis 274a. The spikes 400 can include a porous coated material that is coated onto the spikes 400 and the proximal femoral prosthesis 274. In addition, the spikes 400 can be formed of the porous material, including that discussed above, and sintered or otherwise affixed to the proximal femoral prosthesis 274. In addition, the spikes 400 can be formed on a pad or formed with a pad of the porous material, and the pad of porous material can be sintered or otherwise affixed to the proximal femoral prosthesis 274a to provide the spikes 400. The spikes 400, therefore, can be formed integrally as one piece with the proximal femoral prosthesis 274a, or can be selectively fixed to the proximal femoral prosthesis 274a.

In one example, the spikes 400 can extend at an angle α generally less than 90°, such as about 10° to about 80°. The angle α is defined by an angle formed between the attachment surface 398 and the spikes 400. The spikes 400, at the angle α, generally extend in a direction away from the originating point of the tissue 271. The spikes 400 can therefore pierce the bone 272 at a favorable angle for capturing the tissue 271 at the proximal femoral prosthesis 274.

In addition to the spikes 400, other areas at the attachment region 396 can be formed of a porous material; the first member 394 can also be formed of a porous material. As discussed above, the first member 394 can be coated with a porous material or be formed completely of a porous material. If the first member 394 is formed completely of a porous material, it can be provided to allow for a substantial ingrowth of the bone from the bone portion 272. In addition, the first member 394 can include a depression or bores to allow for cooperation with the spikes 400 extending from the proximal femoral prosthesis 274A. The spikes 400 can be substantially completely tapered or include a substantially straight walled region, similar to the projections 298 discussed above. Accordingly, the first member 394 can cooperate with the spikes 400 in any appropriate manner.

In continued reference to FIG. 14, the proximal femoral prosthesis 274a can have a bore 402. The bore 402 can be threaded to accept the threaded fastener 286. The bore 402 can alternatively be smooth to accept a fastener assembly including the first fastener member 326 that threadably engages the second fastener member 328 on the medial surface of the proximal femoral prosthesis 274.

Figure 15B:
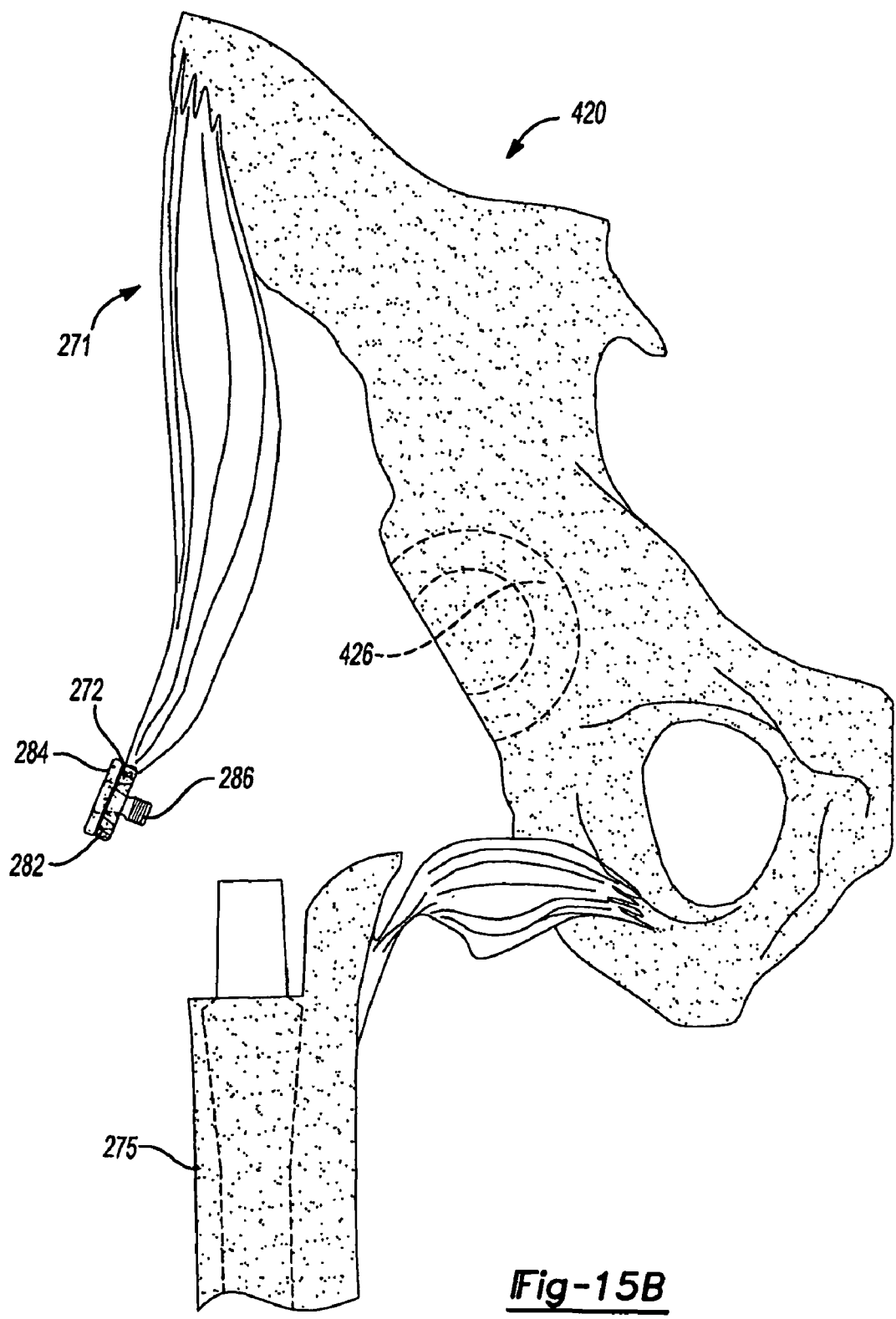
Figure 15C:
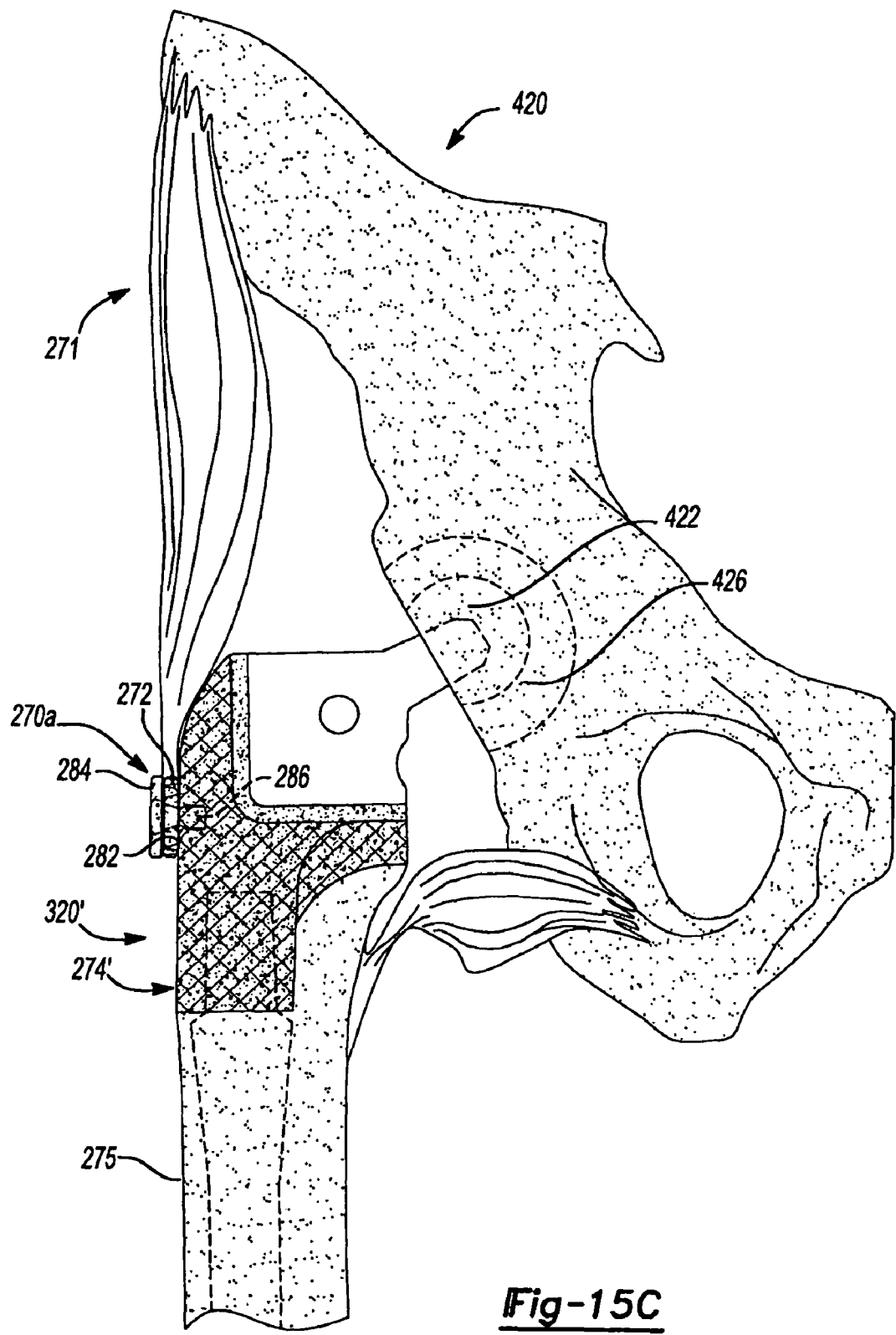

With reference to FIGS. 15A-15C, an exemplary procedure of positioning the proximal femoral prosthesis 274 and attachment assembly, such as the attachment assembly 270a, is illustrated. As generally illustrated in FIG. 15A, the proximal femoral prosthesis 274 can be positioned on a proximal end of the femur 275 to replace a selected portion of the natural femur, including the greater trochanter. The tissue attachment region 320 can substantially replace the greater trochanter of the femur 275. Accordingly, the attachment assembly 270a can be used to interconnect or attach the tissue 271 that extends from a pelvis 420 and attach it to an appropriate region, such as the tissue attachment region 320, of the proximal femoral prosthesis 274. The tissue 271 can be any appropriate tissue to be attached to the femur, including an abductor muscle or tendon.

A user, such as a surgeon, can select any appropriate attachment assembly as discussed herein. Although the attachment assembly 270a including the first member 282 and the second member 284 is discussed in detail, one skilled in the art will understand any appropriate attachment assembly can be used. At the outset, the surgeon can select the first member 282, the second member 284, and fastener 286 for a particular application. Concurrently, the surgeon can select a desired proximal femoral prosthesis 274. The first member 282 can then be positioned adjacent to the attachment region 320 of the proximal femoral prosthesis 274. The bone portion 272 can then be positioned between the outboard face 294 of the first member 282 and the inboard face 296 of the second member 284. The projections 298 can be aligned with the plurality of notches 312. The fastener 286 can be passed through the second aperture 304 of the second member 284, through the bone portion 272, passed through the first aperture 288 of the first member 282 and engaged into the bore 376. As the fastener 286 is progressively engaged into the bore 376, the projections 298 can pierce the bone portion 272 further capturing the bone portion 272 between the first member 282 and the second member 284.

The proximal femoral prosthesis 274 can be positioned within the femur 275 according to any appropriate technique. For example, the proximal femoral prosthesis 274 can be cemented or cementlessly interconnected with the femur 275. In addition, the fastener member 326 can be provided to pass through a portion of the proximal femoral prosthesis 274 and include the second fastener member 328 for fixing the attachment assembly 270a to the proximal femoral prosthesis 274. Nevertheless, the attachment assembly 270a can be interconnected as a unit with the proximal femoral prosthesis 274.

The proximal femoral prosthesis 274 can also be interconnected with a head 422 that is interconnected with a tapered portion 274n of the proximal femoral prosthesis 274. The tapered portion 274n can be interconnected with the femoral head 422 in any appropriate manner. The femoral head 422 can be provided to articulate with a natural acetabulum of the pelvis 420 or an acetabulur implant 426 interconnected with the pelvis 420. It is understood by one skilled in the art that the acetabular prosthesis 426 can be provided in any appropriate manner and be interconnected with the pelvis 420 appropriately. After implantation of the proximal femoral prosthesis 274 including the femoral head 422, it can articulate relative to the acetabular prosthesis 426 in a substantially natural manner. Moreover, the interconnection of the tissue 271 with the proximal femoral prosthesis 274 can allow for substantially natural articulation and strength of the femur 275, even with the proximal femoral prosthesis 274.

At various occasions, however, the proximal femoral prosthesis 274 may require replacement. For example, during revision procedures the proximal femoral prosthesis 274 may be replaced or removed, as illustrated in FIG. 15B. When the proximal femoral prosthesis 274 is removed, the attachment assembly 270a can be removed from the proximal femoral prosthesis 274 together. The fastener 286 may be removed from the first and second members 282, 284, but the first and second members 282, 284 may be retained together due to the boney ingrowth from the bone portion 272. Thus, the bone portion 272 and the first and second members 282, 284 can be maintained as a single unit during a revision or a subsequent procedure.

Once a new or revision proximal femoral prosthesis 274' has been repositioned or implanted into the femur 275, the attachment assembly 270a, as a unit including the first member 282, the second member 284, and the bone portion 272 can be reconnected to the revision proximal femoral prosthesis 274'. The fastener 286 can be the same fastener, a replacement fastener, or a different fastener system to interconnect the attachment assembly 270a with the revision proximal femoral prosthesis 274'. Accordingly, the tissue portion 271 can be substantially reattached to a revision proximal femoral prosthesis 274' without disengaging or removing any of the boney ingrowth into the attachment assembly 270a accomplished during the original implantation procedure. Therefore, a substantially strong fixation of the tissue portion 271 with the proximal femoral prosthesis 274' can be maintained even after the revision procedure. The strong connection of the tissue portion 271 can allow for a faster recovery or greater mobility and use of the femur 275 with the proximal femoral prosthesis 274'.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited, since other modifications will become apparent to the skilled practitioner upon a study of the drawings, the specification and the following claims.

What is claimed is:

1. A femoral prosthesis system having a tissue attachment portion, comprising:
   a proximal femoral prosthesis having a stem portion and a neck portion and configured to replace at least a portion of a proximal portion of a femur that is medial of a greater trochanter of the femur;
   an attachment assembly separate from the proximal femoral prosthesis;
   a first porous metal pad that is generally planar and fixed directly to an inferior surface of a portion of the proximal femoral prosthesis that is on a medial portion of the proximal femoral prosthesis and is extending substantially transverse to a long axis of the femur and where the first porous metal pad is operable to allow boney ingrowth directly into the first porous metal pad directly from a resected proximal surface of the femur; and
   a first fastener operable to interconnect the attachment assembly and the proximal femoral prosthesis.

2. The femoral prosthesis system of claim 1, wherein the attachment assembly has a first surface and a second surface with an aperture defined through the first surface and the second surface, the second surface operable to selectively and removably engage the greater trochanter of the femur with at least a terminal end tip of the attachment assembly, and wherein the second surface includes a second porous metal pad that extends only a portion of a length of the second surface towards the terminal end tip, wherein the second porous metal pad is operable to allow boner ingrowth directly into the second porous metal pad;
   wherein the attachment assembly is configured to allow a tissue portion to be positioned between the attachment assembly and the greater trochanter;
   wherein the second porous metal pad is configured to contact substantially only the tissue portion;
   wherein the first fastener and the second fastener are operable to interconnect the proximal femoral prosthesis and the attachment assembly to fix the tissue portion and the attachment assembly relative to the proximal femoral prosthesis.

3. The femoral prosthesis system of claim 2, wherein the attachment assembly further includes a plurality of extension portions extending from the second surface operable to engage a first side of the tissue portion and operable to extend through at least a portion of the tissue portion.

4. The femoral prosthesis system of claim 2, wherein the fastener has an external thread to threadably engage an internally threaded bore formed in the proximal femoral prosthesis in the interconnected position.

5. The femoral prosthesis system of claim 2, further comprising:
   a second fastener;
   wherein the proximal femoral prosthesis defines a smooth bore;
   wherein the first fastener has an external thread and is operable to pass through the bore defined by the proximal femoral prosthesis and is operable to threadably engage the second fastener on a medial side of the proximal femoral prosthesis in the interconnected position.

6. The femoral prosthesis system of claim 1, wherein the terminal end tip of the attachment assembly further includes a first terminal end tip and a second terminal end tip;
   wherein the first terminal end tip is configured to engage a first portion of the greater trochanter and the second terminal end tip is configured to engage a second portion of the greater trochanter distal the first portion of the greater trochanter;
   wherein a surface of the attachment assembly further includes a second porous metal pad that extends less than an entire distance between the first terminal tip portion and the second terminal tip portion.

7. The femoral prosthesis system of claim 6, wherein attachment assembly is arcuate between the first terminal end tip and the second terminal end tip and the first terminal tip and the second terminal tip are configured to pierce the femur.

8. The system of claim 1, wherein the attachment assembly is formed completely of a porous metal.

9. A femoral prosthesis system having a tissue attachment portion, comprising:
   a proximal femoral prosthesis having a stem portion and a neck portion and configured to replace at least a portion of a proximal portion of a femur that is medial of a greater trochanter of the femur;
   an attachment assembly separate from the proximal femoral prosthesis, the attachment assembly having a first surface and a second surface with an aperture defined through the first surface and the second surface, the attachment assembly further having a first terminal end tip and a second terminal end tip, the second surface operable to selectively and removably engage the greater trochanter of the femur, and wherein the second surface includes a first porous metal pad that extends less than an entire distance between the first terminal end tip and the second terminal end tip of the attachment assembly and is operable to allow boney ingrowth directly into the first porous metal pad; and
   a fastener separate from the proximal femoral prosthesis and the attachment assembly operable to interconnect the attachment assembly and the proximal femoral prosthesis;
   wherein the first porous metal pad of the attachment assembly is operable to directly contact the greater trochanter to allow boney ingrowth directly into the first porous metal pad.

10. The femoral prosthesis system of claim 9,
   wherein attachment assembly is arcuate between the first terminal end tip and the second terminal end tip;
   wherein the first terminal end tip is configured to engage a first portion of the greater trochanter and the second terminal end tip is operable to engage a second portion of the greater trochanter distal the first portion of the greater trochanter.

11. The femoral prosthesis system of claim 10, wherein the first porous metal pad is arcuate and configured to extend to contact the bone portion of the femur and the first terminal tip and the second terminal tip pierce the femur.

12. The femoral prosthesis system of claim 10, wherein a tissue portion is operable to be positioned between at least a portion of the attachment assembly and the greater trochanter;
   wherein at least a portion of the first porous metal pad is configured to contact the tissue portion;
   wherein the fastener interconnects the proximal femoral prosthesis and the attachment assembly to fix the tissue portion and the attachment assembly relative to the proximal femoral prosthesis.

13. The femoral prosthesis system of claim 10, further comprising:
   a second porous metal pad fixed directly to a medial portion of the proximal femoral prosthesis operable to allow boney ingrowth directly into the second porous metal pad directly from a medial portion of the femur;
   wherein the medial portion of the proximal femoral prosthesis is medial of the greater trochanter when the proximal femoral prosthesis is positioned in the femur.

14. The system of claim 13, wherein both the attachment assembly and the second porous metal pad are formed completely of a porous metal.

15. A femoral prosthesis system having a tissue attachment portion, comprising:
   a proximal femoral prosthesis configured to replace at least a proximal portion of a femur of an anatomy;
   an attachment assembly separate from the proximal femoral prosthesis having a first surface and a second surface and an aperture extending between and through the first surface and the second surface, the attachment assembly including a porous metal pad operable to contact a tissue portion wherein the attachment assembly has an arcuate shape terminating in a first end tip and a second end tip wherein the first end tip and the second end tip are both operable to engage the proximal portion of the femur;
   a first fastener operable to hold the attachment assembly and the proximal femoral prosthesis relative to each other and the tissue portion and to capture the tissue portion relative to the proximal portion of the femur; and
   a second fastener;
   wherein the first fastener passes through a first bore formed from a lateral side to a medial side of the proximal femoral prosthesis and a second bore formed in the attachment assembly to threadably engage the second fastener on the medial side of the proximal femoral prosthesis in a coupled position.

16. The femoral prosthesis system of claim 15, wherein the attachment assembly includes a plurality of extension portions formed on the first surface of the attachment assembly and extend in a direction towards the tissue portion, wherein the first surface is formed of the porous metal and the second surface is formed of solid biocompatible metal.

17. The femoral prosthesis system of claim 15, wherein the first fastener has an external thread to threadably engage a threaded portion of the first bore formed in the proximal femoral prosthesis in the coupled position.

18. The femoral prosthesis system of claim 15, wherein the first bore is a smooth bore formed in the proximal femoral prosthesis.

19. The femoral prosthesis system of claim 15, wherein the attachment assembly is formed entirely of a completely porous metal.

20. The femoral prosthesis system of claim 15, further comprising:
   a porous metal pad fixed to the proximal femoral prosthesis to engage the femur and allow direct bone ingrowth into the porous metal pad.

21. The femoral prosthesis of claim 5, wherein the bore is a smooth bore extending from a lateral side to a medial side of the proximal femoral prosthesis.

* * * * *